United States Patent [19]

Nakamura et al.

[11] Patent Number: 5,861,987
[45] Date of Patent: Jan. 19, 1999

[54] STEREOSCOPIC-VISION ENDOSCOPE OFFERING A LARGE ANGLE OF INTROVERSION AND A NECESSARY AND SUFFICIENT SENSE OF THREE-DIMENSIONALITY

[75] Inventors: Shinichi Nakamura; Haruko Magata, both of Tokyo, Japan

[73] Assignee: Olympus Optical Co., Ltd., Tokyo, Japan

[21] Appl. No.: 518,490

[22] Filed: Aug. 23, 1995

[30] Foreign Application Priority Data

| Aug. 30, 1994 | [JP] | Japan | 6-205704 |
| Dec. 27, 1994 | [JP] | Japan | 6-337018 |
| May 23, 1995 | [JP] | Japan | 7-124104 |

[51] Int. Cl.$^6$ ............ G02B 27/02; G02B 3/00; G02B 17/00; G02B 9/12
[52] U.S. Cl. .......... 359/434; 359/435; 359/654; 359/735; 359/737; 359/784; 359/738; 359/674; 359/429; 359/441
[58] Field of Search ............. 359/434, 435, 359/654, 735, 737, 784, 738, 676, 677, 678, 429, 441

[56] References Cited

U.S. PATENT DOCUMENTS

| 3,994,557 | 11/1976 | Hopkins | 359/374 |
| 4,515,444 | 5/1985 | Prescott et al. | 359/654 |
| 4,615,333 | 10/1986 | Taguchi | 128/6 |
| 4,822,151 | 4/1989 | Tatsuno et al. | 359/495 |
| 4,905,082 | 2/1990 | Nishigaki et al. | 358/98 |
| 5,005,957 | 4/1991 | Kanamori et al. | 359/708 |
| 5,206,759 | 4/1993 | Ono et al. | 359/434 |
| 5,233,473 | 8/1993 | Kanamori | 359/708 |
| 5,508,846 | 4/1996 | Hall | 359/643 |

FOREIGN PATENT DOCUMENTS

| 93 02 898.9 | 6/1993 | Germany . |
| 92 17 980.0 | 7/1993 | Germany . |

*Primary Examiner*—Davis L. Willis
*Assistant Examiner*—Mohammad Y. Sikder
*Attorney, Agent, or Firm*—Armstrong, Westerman, Hattori, McLeland & Naughton

[57] ABSTRACT

A stereoscopic-vision endoscope of the present invention comprises a tubular elongated insertional part, an objective optical system situated in the insertional part, a relay optical system situated in the insertional part for transmitting an object image formed by the objective optical system, a pupil dividing stop for dividing a light beam emanating from an object image formed by the relay optical system into a plurality of portions, an image formation optical system for receiving light beams from the pupil dividing stop so as to form a plurality of object images having parallax, and imaging devices for picking up the object images formed by the image formation optical system. The relay optical system satisfies the condition $\phi^2/L>0.43$ (where $\phi$ denotes an outer diameter of a system of relay lenses, and L denotes a relay length of the relay optical system).

14 Claims, 22 Drawing Sheets

——— OPTICAL AXIS OF A LEFT-EYE VIEW
—·—·— OPTICAL AXIS OF A COMMON OPTICAL SYSTEM
—··—··— OPTICAL AXIS OF A RIGHT-EYE VIEW

STEREOSCOPIC-VISION ENDOSCOPE OFFERING A LARGE ANGLE OF INTROVERSION AND A NECESSARY AND SUFFICIENT SENSE OF THREE-DIMENSIONALITY

BACKGROUND OF THE INVENTION

1. Field of the Invention

The present invention relates to a stereoscopic-vision endoscope enabling stereoscopic observation of an object.

2. Description of the Related Art

In resent years, it has prevailed in the field of surgery to adopt an endoscopic approach instead of laparotomy. Specifically, the inside of an abdomen is observed by creating a small orifice in the abdomen and then inserting a rigid endoscope through the orifice. If necessary, the rigid endoscope is used in combination with a TV camera, so that a therapeutic instrument can be advanced for the purpose of surgery while viewing a monitor.

The rigid endoscope is usually used to provide a view of the inside of a body cavity as a plane image not giving depth perception. It is therefore difficult to observe fine irregularity on the surfaces of inner walls of a body cavity. Since depth information is unavailable, it takes too much time to complete surgery. For solving this problem, a stereoscopic-vision endoscope offering depth information has been developed recently.

The stereoscopic-vision endoscope is classified into two types. One of the types has two optical systems arranged in parallel with each other. Images provided by the optical systems are formed on imaging devices or the like. This type is referred to as a dual-relay type. The other type of stereoscopic-vision endoscope has an optical system at the distal end thereof. A light beam is divided at the position of exit-pupil formation. Images having parallax are formed on imaging devices or the like. This type is referred to as a pupil-division type.

In the dual-relay type endoscope, each of the optical systems has a large number of lenses. It is therefore hard to minimizing a difference between images provided by two optical systems. As far as the stereoscopic-vision rigid endoscope is concerned, the pupil-division type is more effective than the dual-relay type.

With the spread of such a stereoscopic-vision rigid endoscope, there is a growing need for a stereoscopic-vision rigid endoscope to be used for observation of fine regions including the brain and the inside of an eye. For observing the fine regions including the brain and the inside of an eye, it is a must that the stereoscopic-vision rigid endoscope has a thin insertional part.

Described in Germany Patent No. 9302898.9 is regarded as a conventional endoscope of the pupil-division type enabling stereoscopic visioning and having two optical systems. This endoscope is, as shown in FIG. 36, composed of an objective lens 121, an image transmission optical system 122, an image formation optical system 123, and a main objective lens 124, which share a common optical axis.

In this conventional endoscope, the main objective lens 124 is a system of lenses for forming an intermediate image I1 by converging light to infinity. An aperture stop 125 having two apertures is placed behind (at the position of an exit pupil of) the main objective lens 124. Beams confined by the aperture stop 125 pass through imaging optical systems 126a and 126b, and form images on imaging devices 127a and 127b, whereby a three-dimensional image is produced.

It is also described in the Germany patent publication that if the image transmission optical system 122 is realized with a refractive index distribution type lens, a thinner endoscope can be realized.

The aforesaid conventional endoscope has not been described to have the configuration permitting a proper sense of three-dimensionality and proper brightness which are required for stereoscopic visioning while realizing a thinner endoscope.

Another optical system for a conventional endoscope enabling stereoscopic visioning has been described in Japanese Patent Laid-Open No. 6-59199 shown in FIG. 37. This optical system is a single optical system composed of an objective optical system 200 and a relay optical system 201 which are axially symmetric. An image formed by the objective optical system 200 is transmitted by a predetermined distance by the relay optical system 201. A prism 202 is placed at the back end of the relay optical system 201, whereby an exit pupil is spatially divided into two portions so that a pair of right and left images having parallax can be picked up by imaging means 203 and 204 such as CCDs. The pair of right and left images thus picked up is converted into electric signals and displayed on a TV monitor that is not shown. At this time, when the right and left images to be displayed are switched at a high speed and shutter glasses whose movements are synchronous with the switching are employed, a right-eye image is viewed by a right eye and a left-eye image is viewed by a left eye. This results in stereoscopic visioning.

These types of objective and relay optical systems have the same structure as those employed in any conventional endoscope that is not designed for stereoscopic visioning. Many components contribute to formation of both the right and left light paths. Owing to the limited number of components, manufacturing errors are limited and assembling efficiency is excellent.

As for the stereoscopic-vision endoscope described in the Japanese Patent Laid-Open No. 6-59199, the degree of parallax is too low to provide a sufficient sense of three-dimensionality. This point will be described in conjunction with FIG. 38.

An image I' formed by the objective optical system 200 is transmitted by the relay optical system 201. Thereafter, a beam is divided into two portions by a pupil dividing means 206. Images are then formed on imaging devices 208a and 208b by means of right and left image formation optical systems 207a and 207b. The pupil dividing means 206 is composed of a pupil formation lens 210 for receiving a light beam emanating from a final image Ie of the relay optical system and then converging the light beam to infinity, a pupil dividing stop 211 for limiting the light beam and dividing it into two portions, and prisms 212a and 212b for extending a space between right and left light beams.

The pupil dividing stop 211 lies substantially at the position of an exit pupil and has apertures 211a and 211b at positions substantially mutually symmetric with respect to the optical axis of the relay optical system 201. Only the light beams (hatched areas in FIG. 38) passing through the apertures 211a and 211b contribute to image formation, and form two exit pupils as images provided by the objective optical system 200.

The relay optical system 201 includes one system of relay lenses or a plurality of systems of relay lenses. Each system of relay lenses is an afocal optical system that has lenses, which have substantially the same focal length and structure, mutually coupled with their focal points aligned and that offers a zero power.

The degree of parallax that is a main factor dominating a sense of three-dimensionality is expressed using an angle of introversion α.

Assuming that a numerical aperture in the object space determined by the objective optical system 200 and relay optical system 201 is NAo, the diameter of an incident image is a, and a spacing between centers of gravity of two entrance pupils of the pupil dividing stop 211 is b, the angle of introversion α is expressed as follows:

$$\alpha = 2k \cdot NAo \ (rad) \quad (1)$$

where k denotes a pupil dividing ratio and equals to a quotient of b/a, and NAo=sin θ=θ is established. Assuming that the para-axial power of the objective optical system 100 is β and the numerical aperture of the relay optical system is NAr, the expression below is established.

$$NAo = \beta \cdot NAr \quad (2)$$

The para-axial power β is expressed as follows under the condition that the distortion of the objective optical system is ignored:

$$\beta = \frac{I'}{I} = \frac{I'}{S \cdot \tan\omega}$$

where I denotes the height of an object, I' denotes the height of an image or image height, S denotes a distance from the object, and ω denotes a half angle of view.

Assuming that the focal length of one of the systems of relay lenses is f and the external diameter thereof is φ, the numerical aperture of the relay optical system 101, NAr, is provided as the expression below.

$$NAr = \frac{\phi}{2f}$$

The focal length of one of the systems of lenses is a focal length of one front or back part of the relay optical system (that is one system of relay lenses regarded as the unit of a relay) with respect to the position of entrance-image formation. Herein, the focal length of the front part of the relay optical system is not equal to the one of the back part thereof.

When the image height I' is expressed as a ratio relative to the external diameter φ of the relay optical system, the following expression is given:

$$I' = n\phi$$

where n denotes a ratio of the image height to the external diameter φ.

When the focal length f of one of the systems of relay lenses is expressed as a ratio relative to the length of a relay or relay length L, the following expression is provided:

$$f = mL$$

where m denotes the ratio of the focal length to the relay length L.

By combining the aforesaid expressions, the angle of introversion α is rewritten as follows:

$$\alpha = \frac{k \cdot n}{m} \cdot \frac{1}{S \cdot \tan\omega} \cdot \frac{\phi^2}{L} \quad (3)$$

Table 1 lists the values of the angle of introversion α calculated according to the expression (3) in consideration of the specifications of conventional stereoscopic-vision endoscopes. The specifications of first and second conventional stereoscopic-vision endoscopes are excerpted from Germany Utility Model Unexamined Publication No. G9302898.2. Herein, the pupil dividing ratio k is 0.75.

[TABLE 1]

| Unit | Item | Symbol | First conventional endoscope | Second conventional endoscope |
|---|---|---|---|---|
| Objective optical system | Angle of view | 2ω | 45° | 60° |
| | Distance from an object | S | 45.2 mm | 46 mm |
| | Image height | I' | 3.34 mm | 3.25 mm |
| Relay optical system | Outer diameter | φ | 7 mm | 7 mm |
| | Numerical aperture | NAr | 0.1 | 0.1 |
| | Squared outer diameter-to-relay length ratio | φ²/L | 0.42 | 0.42 |
| | Outer diameter-to-relay length ratio | φ/L | 0.06 | 0.06 |
| | Focal length-to-relay length ratio | f/L | 0.3 | 0.3 |
| Pupil dividing stop | Dividing ratio | k | 0.75 | 0.75 |
| Whole system | Angle of introversion | α | 1.6° | 1.1° |

The angle of introversion required for providing a necessary and satisfactory sense of three-dimensionality ranges from about 2° to 7°. When the angle of introversion ranges from 1° to 2°, a viewer has an insufficient sense of three-dimensionality. When the angle of introversion is less than 1°, a viewer has almost no sense of three-dimensionality. When the angle of introversion exceeds 7°, a viewer has an excessive sense of three-dimensionality or fails to have a stereoscopic vision and feels fatigued.

As seen from Table 1, the angle of introversion α of the first conventional stereoscopic-vision endoscope is 1.6° with the endoscope separated from an object by the best distance. A viewer has a slight sense of three-dimensionality but does not have a sufficient sent thereof. In this case, the angle of view is as small as 45° and makes the endoscope unsuitable for surgical use through endoscopic observation.

The second conventional stereoscopic-vision endoscope has an angle of view of 60°. The angle of introversion is as small as 1.1° with the endoscope separated from an object by the best distance. With this value of the angle of introversion, the object cannot be discerned three-dimensionally in practice.

FIG. 39 is a graph of an angle of introversion, which is calculated according to the expression (3), versus a distance from an object. The angle of introversion provided by the second conventional endoscope under the condition of ($\phi^2$/L)=0.42 as well as the one provided thereby under the condition of ($\phi^2$/L)=0.82 are also indicated graphically. Assuming that an angle of introversion permitting even a slight sense of three-dimensionality is 1° or more and an angle of introversion not resulting in an excessive sense of three-dimensionality is 7° or less, the distance from an object that can be viewed three-dimensionally ranges from 10 to 50 mm in the case of the second conventional endoscope. Stereoscopic vision is confined to a limited space. The angle of introversion relative to the best distance from an object, 46 mm, is about 1°, providing substantially no sense of three-dimensionality. When the angle of view ω in the expression (3) is set to a small value, the angle of introversion α becomes larger. Nevertheless, the angle of view, 45°, provides an insufficient sense of three-dimensionality for practical use.

OBJECTS AND SUMMARY OF THE INVENTION

An object of the present invention is to provide a stereoscopic-vision endoscope capable of offering a large angle of introversion without reducing an angle of view and providing a necessary and sufficient sense of three-dimensionality over a wide area.

Another object of the present invention is to provide a small-diameter stereoscopic-vision endoscope offering an appropriate sense of three-dimensionality and permitting necessary and sufficient brightness even on the perimeter of a visual field.

A stereoscopic-vision endoscope of the present invention comprises a tubular elongated insertional part, an objective optical system situated in said distal portion of the insertional part, a relay optical system situated in said insertional part for transmitting an image of an object or an object image formed by said objective optical system, a pupil dividing means for dividing a light beam emanating from said object image formed by said relay optical system into a plurality of portions, an image formation optical system for receiving the light beam from said pupil dividing means and forming a plurality of object images having parallax, and an imaging means for picking up the object images formed by said image formation optical system. Said relay optical system includes a system of relay lenses satisfying the condition of $\phi^2$/L>0.43 (where $\phi$ denotes the outer diameter of the system of relay lenses and L denotes the relay length of the relay optical system), whereby an angle of introversion can be increased without the need of reducing an angle of view, and a necessary and sufficient sense of three-dimensionality can be offered.

Other features and advantages of the present invention will be fully apparent from the description below.

BRIEF DESCRIPTION OF THE DRAWINGS

FIG. 1 shows the overall configuration of a stereoscopic-vision endoscope system having a stereoscopic-vision endoscope;

FIG. 2 shows the components of an imaging optical system in the stereoscopic-vision endoscope shown in FIG. 1;

FIG. 3 is a first sectional view showing a section of a system of relay lenses in the insertional part shown in FIG. 2 in relation of the positions of entrance pupils;

FIG. 4 is a second sectional view showing a section of the system of relay lenses in the insertional part shown in FIG. 2 in relation to the positions of entrance pupils;

FIG. 5 is a graph showing the relationship of the ratio of an angle of introversion ($\alpha_2$/$\alpha_1$) with the ratio of an outer diameter of a system of relay lenses shown in FIG. 3;

FIG. 6 is a first explanatory diagram concerning a first variant of the pupil dividing stop in FIG. 2;

FIG. 7 is a second explanatory diagram concerning the first variant of the pupil dividing stop in FIG. 2;

FIG. 8 is a first explanatory diagram concerning a second variant of the pupil dividing stop in FIG. 2;

FIG. 9 is a second explanatory diagram concerning the second variant of the pupil dividing stop in FIG. 2;

FIG. 10 is a third explanatory diagram concerning the second variant of the pupil dividing stop in FIG. 2;

FIG. 11 shows the components of a variant of an imaging optical system in the stereoscopic-vision endoscope shown in FIG. 1;

FIG. 16 shows the route of rays traveling within the refractive index distribution type lens shown in FIG. 15;

FIG. 17 is a graph showing the relationship of the image height in the refractive index distribution type lens shown in FIG. 15 with the ratio of a numerical aperture;

FIG. 18 shows the vicinity of rays emanating from a point of a maximum image height and residing on a section of a light beam located near the positions of entrance pupils formed by the refractive index distribution type lens shown in FIG. 15;

FIG. 19 shows the vicinity of rays traveling at a maximum image height along the optical axis of the refractive index distribution type lens shown in FIG. 15 from the vicinity of the positions of entrance pupils;

FIG. 20 shows the shape of a pupil dividing stop situated at a position conjugate to the positions of entrance pupils formed by the refractive index distribution type lens shown in FIG. 15;

FIG. 21 is a first diagram showing the relationship of the section of a light beam located near the positions of entrance pupils formed by the refractive index distribution type lens shown in FIG. 15 with the pupil dividing stop;

FIG. 22 is a second diagram showing the relationship of the section of a light beam located near the positions entrance pupils formed by the refractive index distribution type lens shown in FIG. 15 with the pupil dividing stop;

FIG. 23 is a first diagram showing the relationship of the apertures of the pupil dividing stop with the angle of introversion for an optical system including the refractive index distribution type lens shown in FIG. 15;

FIG. 24 is a second diagram showing the relationship of the apertures of the pupil dividing stop with the angle of introversion for an optical system including the refractive index distribution type lens shown in FIG. 15;

FIG. 25 shows the particular configuration of a system including a stereoscopic-vision rigid endoscope of the fourth embodiment;

FIG. 26 shows the components of an optical system for the stereoscopic-vision rigid endoscope shown in FIG. 25;

FIG. 27 is a sectional view showing a light beam in relation to the positions of exit pupils near which a pupil dividing means of the optical system shown in FIG. 26 is situated; and FIG. 28 shows part of the components of an optical system for a stereoscopic-vision rigid endoscope for skew vision that is a variant of the fourth embodiment;

DETAILED DESCRIPTION OF THE PREFERRED EMBODIMENTS

Figure 1:
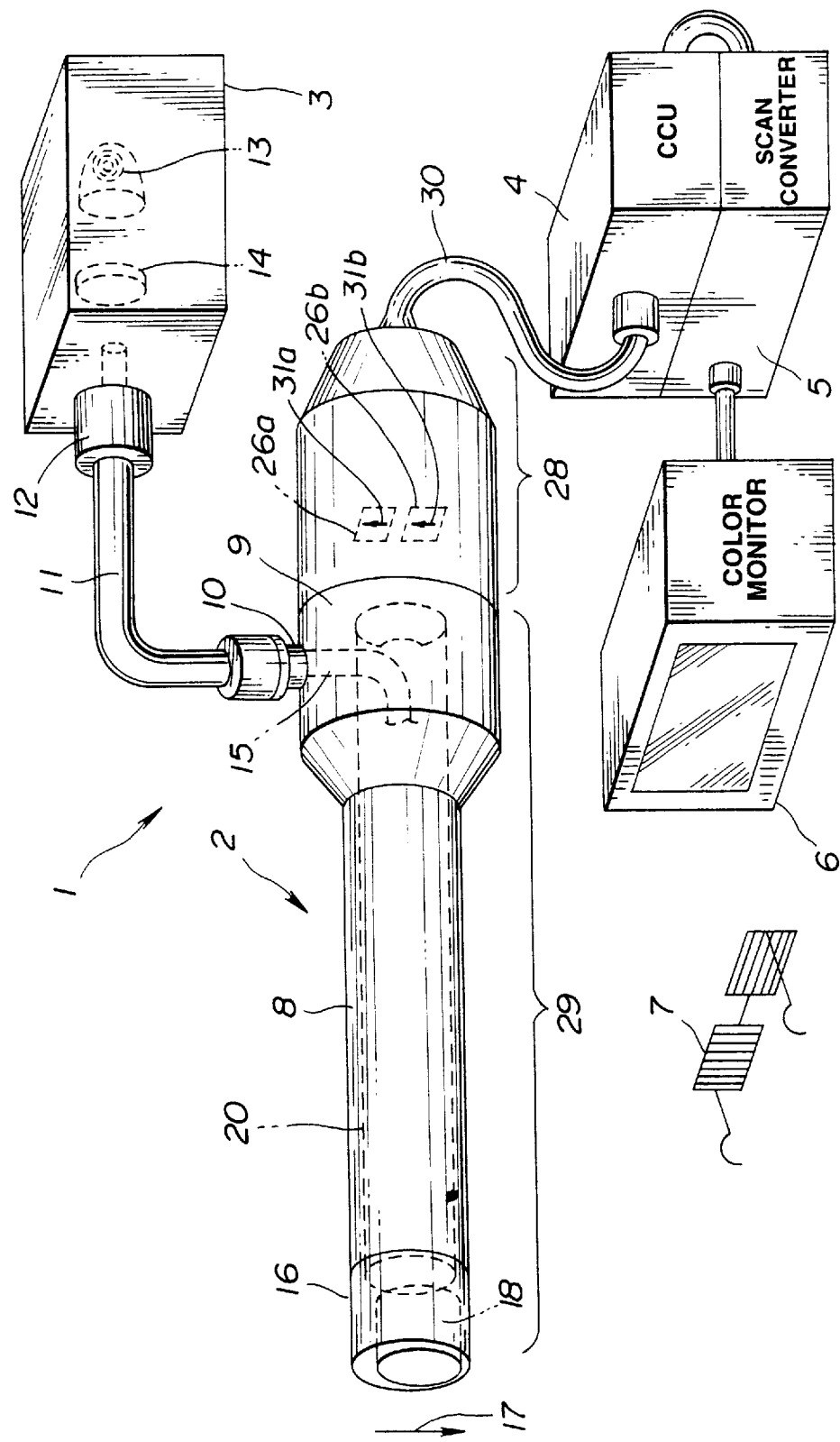
FIGS. 1 to 11 relate to the first embodiment.

Referring to the drawings, embodiments of the present invention will be described in detail.

As shown in FIG. 1, a stereoscopic-vision endoscope system 1 comprises a stereoscopic-vision endoscope 2 of the first embodiment having a built-in imaging optical system enabling stereoscopic visioning, a light source unit 3 included in the stereoscopic-vision endoscope 2 for feeding illumination light to an illumination light transmitting means for transmitting illumination light, a camera control unit 4 (hereinafter CCU) for processing signals sent from an imaging means incorporated in the stereoscopic-vision endoscope 2, a scan converter 5 for converting a signal provided by the CCU 4 into a video signal, a color monitor 6 for displaying a video signal provided by the scan converter 5, and shutter glasses 7 having the capability of a shutter and assisting in discerning an image appearing on the color monitor 6 three-dimensionally.

The stereoscopic-vision endoscope 2 includes an elongated insertional part 8 to be inserted into a body cavity, and a grip 9 formed at the back end of the insertional part 8, shaped to have a larger diameter than the insertional part 8, and designed to be gripped by an operator. The insertional part 8 is tubular and realized with a rigid armor tube made of a metal such as stainless steel. In short, the stereoscopic-vision endoscope 2 is a rigid endoscope having the rigid insertional part 8.

The stereoscopic-vision endoscope 2 includes, similarly to an ordinary endoscope, an illumination light transmission means for transmitting illumination light supplied from the light source unit 3, an illumination optical system for emitting the transmitted illumination light through an illumination window so as to illuminate an object, and an observation optical system (imaging optical system) for providing two views having parallax so that an object illuminated by the illumination optical system can be viewed three-dimensionally.

This embodiment is described in terms mainly of a stereoscopic-vision endoscope exerting the effect of forming two images having parallax on imaging devices that have the capacity for photoelectric transformation and serve as the observation optical system. The observation optical system may be referred to as an imaging optical system.

The grip 9 has a light guide base 10. One end of a light guide cable 11 is detachably coupled to the light guide base 10. A light guide connector 12 at the other end of the light guide cable 11 is detachably coupled to the light source unit 3.

Incorporated in the light source unit 3 are a lamp 13 for generating white illumination light and a lens 14 for converging the white light. Illumination light converged by the lens 14 is irradiated to an end surface of the light guide connector 12. The illumination light irradiated to the end surface is transmitted over a light guide lying through the light guide cable 11. The transmitted illumination light is fed to a light guide 15 inside the stereoscopic-vision endoscope 2.

The light guide 15 serving as an illumination light transmitting means is angled inside the grip 9 and routed through the insertional part 8. The light guide 15 transmits supplied illumination light, and emits the illumination light forward through a distal surface fixed to a distal section 16 of the insertional part 8.

Figure 2:
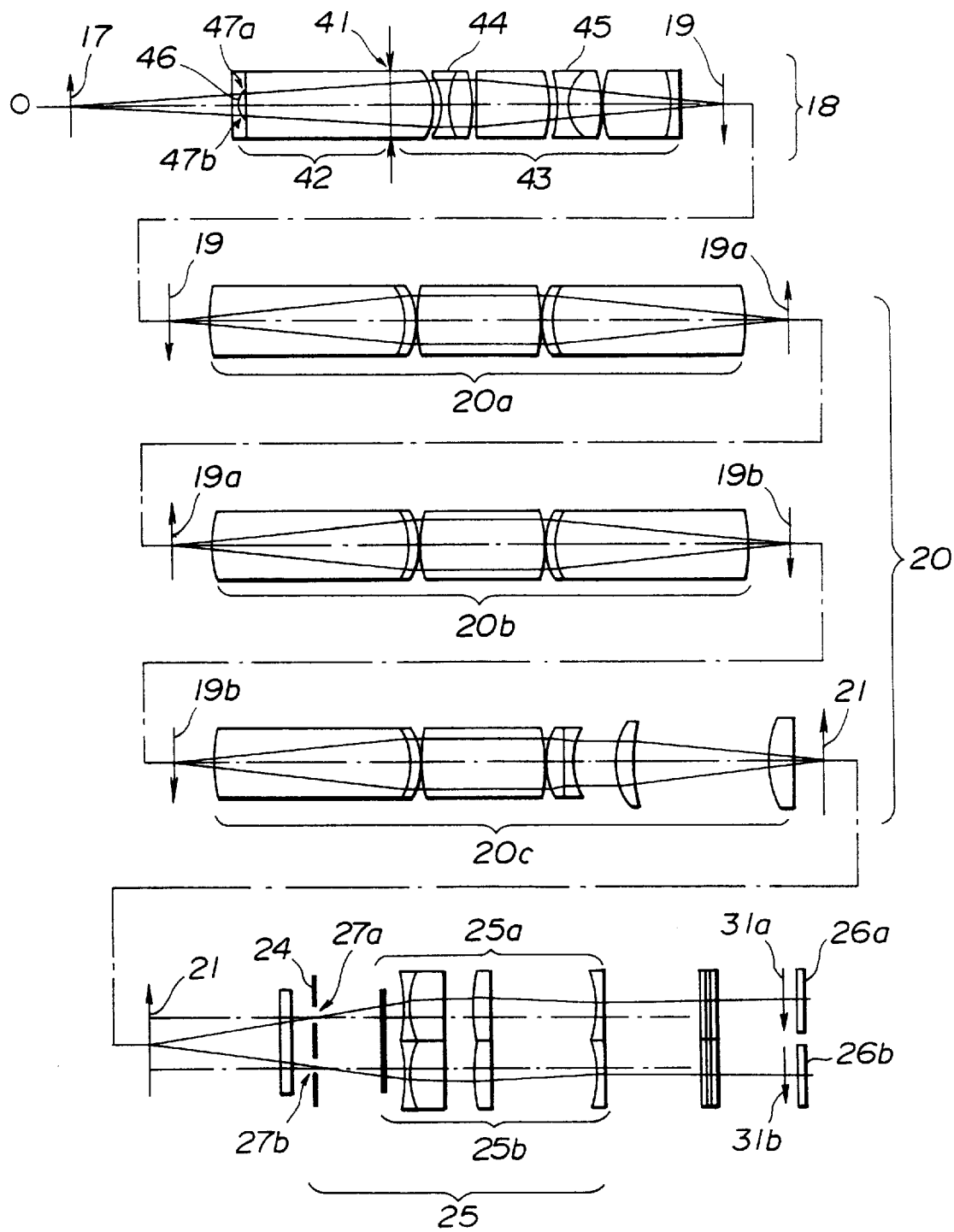

In the imaging optical system, an object 17 (indicated with an arrow in FIG. 1) illuminated with the illumination light is imaged by an objective optical system 18 attached to an observation window adjoining an illumination window in the distal section 16. Consequently, as shown in FIG. 2, an optical image 19 is formed at a position of image formation. The image 19 is transmitted backward by means of a relay optical system 20. A light beam carrying a final image 21 provided by the relay optical system 20 is divided into two portions by a pupil dividing stop 24 (pupil dividing means), and finally converged on photoelectric transformation (imaging) surfaces of imaging devices 26a and 26b (imaging means) incorporated in the grip 9.

According to the configuration of the present invention, a main light beam emanating from the center of a relayed final image 21 and passing through the middles of two apertures 27a and 27b of the pupil dividing stop 24 is emitted askew through an image formation lens 25. Thus, the distance from the relayed final image 21 to the imaging surfaces are very short and the hand-held unit is designed compactly. The image formation lens 25 is composed of right and left image formation lenses 25a and 25b having independent optical axes respectively. The pupil dividing stop 24 has not only the ability to divide a light beam into two portions but also the ability to restrict the sizes of apertures (brightness). The pupil dividing stop 24 may therefore be referred to as a brightness stop.

Returning to FIG. 1, it is seen that the imaging devices 26a and 26b have, for example, square imaging surfaces. The lengths or widths of the imaging surfaces are oriented in the direction in which the two apertures 27a and 27b of the pupil dividing stop 24 shown in FIG. 2 are placed side by side with a space between them.

The grip 9 includes an output unit 28 having the image formation optical system 25 and imaging devices 26a and 26b, and an input unit 29 lying ahead of the output unit 28, which are freely detachable. The input unit 29 includes the objective optical system 18 and relay optical system 20.

Since the output unit 28 is designed to be detachable, repair can be carried out readily in case the imaging devices 26a and 26b fail. Moreover, a structure having flexibility can be realized so that performance can be improved by selectively employing high-sensitivity imaging devices or imaging devices having a large number of pixels or by selectively employing input units that provide visual fields of different orientations or angles. When mounted, the input and output units can be turned about the optical axis of the relay optical system so that the orientation of an image can be corrected.

The imaging devices 26a and 26 are connected to the CCU 4 over a signal cable 30 extending from the back end of the output unit 28. Image signals photoelectrically transformed by the imaging devices 26a and 26b are subjected to signal processing. The image signals subjected to signal processing by the CCU 4 are fed to the scan converter 5, converted into video signals, and then supplied to the color monitor 6. Images having parallax and being formed separately due to the two apertures 27a and 27b of the pupil dividing stop 24 are displayed alternately on the color monitor 6. By viewing the images on the color monitor 6 using the shutter glasses 7, an operator discerns a three-dimensional image.

As shown in FIG. 2, the imaging optical system in the stereoscopic-vision endoscope of the first embodiment comprises the objective optical system 18, relay optical system 20, pupil dividing stop 24, image formation optical system 25, and imaging devices 26a and 26b which are arranged in that order starting from the outermost object space. As described previously, the objective optical system 18 forms the image 19. The image 19 is reformed into a plurality of images 19a and 19b by means of systems of relay lenses 20a, 20b, and 20c, which constitute the relay optical system 20 and lie in series with one another so that the optical axes O thereof will align with one another, and thus relayed with a zero power. A light beam emanating from a transmitted final image 21 is divided by the pupil dividing stop 24. Two images 31a and 31b having parallax are formed on the imaging devices 26a and 26b by means of the image formation lenses 25a and 25b.

The objective optical system 18 consists of a group of concave lenses 42 lying in the object space beyond a virtual stop 41 and a group of convex lenses 43 lying in the image space beyond it. The group of convex lenses 43 includes meniscus lenses 44 and 45. The meniscus lens 44 has the concave surface thereof in the object space so as exert the effects of reducing the heights of rays at the position of the virtual stop 41 and of increasing the amount of ambient light by minimizing the angles of main rays. This structure is quite effective for a variant using a skew-vision prism that will be described later. The meniscus lens 45 exerts the effect of causing the objective optical system 18 to generate positive field-curvature aberration so as to cancel out field-curvature aberration occurring in the relay optical system 20.

The fourth surface of the objective optical system 18 is an aspheric plane for correcting distortion occurring in the objective optical system 18. Normally, the aspheric plane is used as a convex surface (third surface) of a distal concave lens of the objective optical system, on which the height of main rays become maximum, for the purpose of correcting distortion. In this embodiment, the third surface of the distal concave lens is a flat plane. An aspheric plane is used as a concave surface in the image space (the aspheric conditions for the fourth surface are such that R=5.0, P=1.0, $A_4=0.53376 \cdot 10^{-3}$, $A_6=-0.80576*10^{-4}$, and $A_8=-0.19333*10^{-5}$, where; '*' means multiplication). The fourth surface has a curvature decreasing gradually from the optical axis toward the perimeter. As a result, the heights of perimetric rays on the third surface are smaller. The aspheric-surface lens 46 has therefore a small outer diameter. This constituent feature has a significant meaning when a bright objective optical system (f-number of 2.7) employed in this embodiment is used to make the orientation of a visual field askew.

In this embodiment, the number of relays is three. Alternatively, the n umber of relays may range from one to several tens depending on the specifications including the length and diameter of the insertional part 8 and the brightness of an optical system.

In FIG. 2, reference numerals 47a and 47b denote positions of entrance pupils of the pupil dividing stop 24 provided by the objective optical system 18. Incident light passing the positions of the entrance pupils 47a and 47b forms right and left images 31a and 31b on the imaging devices 26a and 26b. The positions of the entrance pupils 47a and 47b are conjugate to the position of the pupil dividing stop 24.

In the stereoscopic-vision endoscope 2 of this embodiment, the outer diameter of the insertional part is made very small, while the outer diameter of the relay optical system 20 is made large. While brightness is kept unchanged, an angle of introversion is increased without the need of diminishing an angle of view. This results in an intense sense of three-dimensionality. This technique will be described in conjunction with FIGS. 3 and 4.

Figure 3:
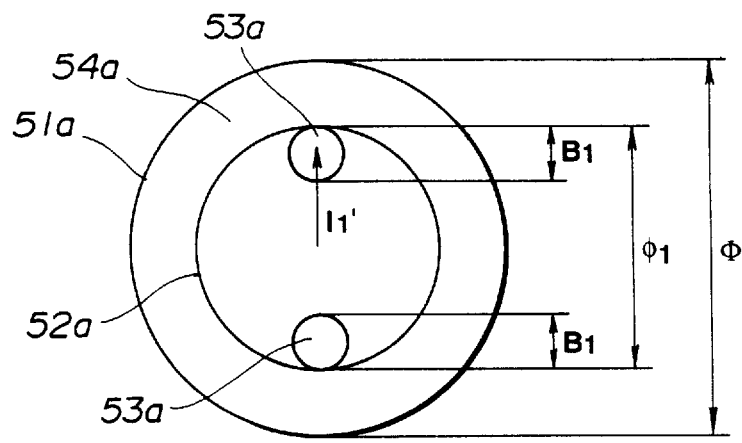
Figure 4:
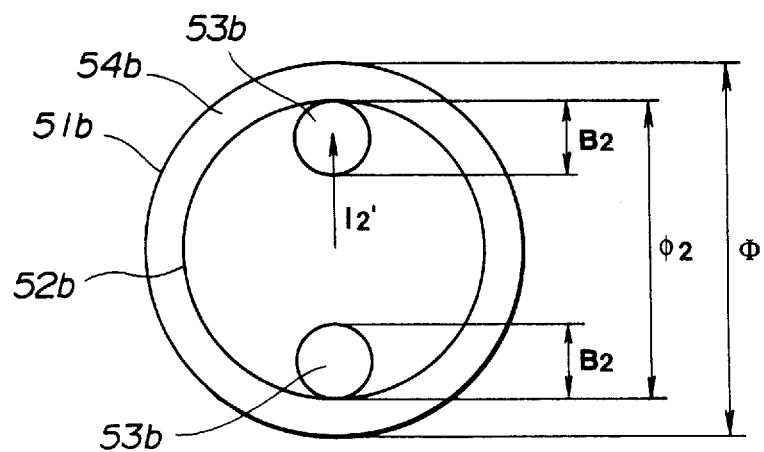

FIGS. 3 and 4 show sections of the systems of relay lenses 20a and 20b in the insertional part 8 in relation to the positions of the entrance pupils. The outer diameters of the armor tubes 51a and 51b of the insertional part shall be Φ, the outer diameters of the systems of relay lenses 20a and 20b shall be $\phi_1$ and $\phi_2$, and the diameters of the right and left entrance pupils 53a and 53b dependent on the apertures of the pupil dividing stop shall be $B_1$ and $B_2$. The positions of the entrance pupils formed by the relay optical system are confined to the diameters of the systems of relay lenses. Light guides pass through the interspace 54a or 54b between the systems of relay lenses 20a and 20b and an armor tube 51a or 51b. For brevity's sake, no consideration will be taken into the thicknesses of the armor tubes and the other components. FIG. 3 shows a prior art in which the ratio (occupancy ratio) of the outer diameter of the system of relay lenses to the outer diameter of the insertional part is small. Many light guides are included. FIG. 4 shows this embodiment in which the outer diameter of the insertional part is the same as that shown in FIG. 3, the occupancy ratio of the system of relay lenses is made larger in order to reduce the number of light guides. A decrease in brightness resulting from the reduced number of light guides is compensated for by enlarging the apertures of the pupil dividing stop, making the diameter of the right entrance pupil $B_2$ larger than that of the left entrance pupil $B_1$, and increasing the height of an image or image height $I_2'$ ($I_2'>I_1'$) by a value corresponding to an increase in outer diameter of the systems of relay lenses.

When the total brightness provided by the illumination system and observation system inclusive is the same between the cases of FIGS. 3 and 4, this embodiment permits a larger angle of introversion than the prior art. The underlying idea will be described below.

Since the amount of illumination light is proportional to the area of a section of a light guide, the ratio of the amount of light in the case of FIG. 4 to that of FIG. 3 is expressed as follows:

$$\frac{\pi(\Phi/2)^2 - \pi(\phi_2/2)^2}{\pi(\Phi/2)^2 - \pi(\phi_1/2)^2} = \frac{\Phi^2 - \phi_2^2}{\Phi^2 - \phi_1^2} = \frac{1-(\kappa\phi_1/\Phi)^2}{1-(\phi_1/\Phi)^2}$$

where $\phi_2 = \kappa \cdot \phi_1$ is established.

A decrease in brightness caused by a light guide is compensated for by increasing the diameters of the right and left entrance pupils and also increasing the image height. The brightness of the observation optical system is proportional to the areas of the right and left entrance pupils and the area of an image, and the image height is proportional to the outer diameters of systems of relay lenses. Under these conditions, the expression below is provided.

$$\frac{B_2^2}{B_1^2} \cdot \frac{\phi_2^2}{\phi_1^2} = \frac{1-(\phi_1/\Phi)^2}{1-(\kappa\phi_1/\Phi)^2}$$

At this time, a pupil dividing ratio k is expressed as follows:
$k_1 = 1 - B_1/\phi_1$
$k_2 = 1 - B_2/\phi_2 = 1 - B_2/(\kappa\phi_1)$ According to the expression (3), the angle of introversion $\alpha$ is proportional to the pupil dividing ratio k and the squares of the outer diameters $\phi$ of the systems of relay lenses. The ratio of the angle of introversion in the case of FIG. 4 to that of FIG. 3 is provided as the expression below.

$$\frac{\alpha_2}{\alpha_1} = \frac{k_2}{k_1} \cdot \frac{\phi_2^2}{\phi_1^2} = \frac{k_2}{k_1} \cdot \kappa^2 = \frac{1}{k_1} \left( \kappa^2 - \frac{B_1}{\phi_1} \sqrt{\frac{1-(\phi_1/\Phi)^2}{1-(\kappa\phi_1/\Phi)^2}} \right)$$

Assuming that the occupancy ratio of a conventional system of relay lenses, $\phi_1/\Phi$, is 0.7 and the antecedent of the pupil dividing ratio, $k_1$, is equal to $1 - B_1/\phi_1 = 0.75$, the expression below is established.

$$\frac{\alpha_2}{\alpha_1} = \frac{4\kappa^2}{3} = \frac{1}{3}\sqrt{\frac{0.51}{1 - 0.49\kappa^2}}$$

Figure 5:
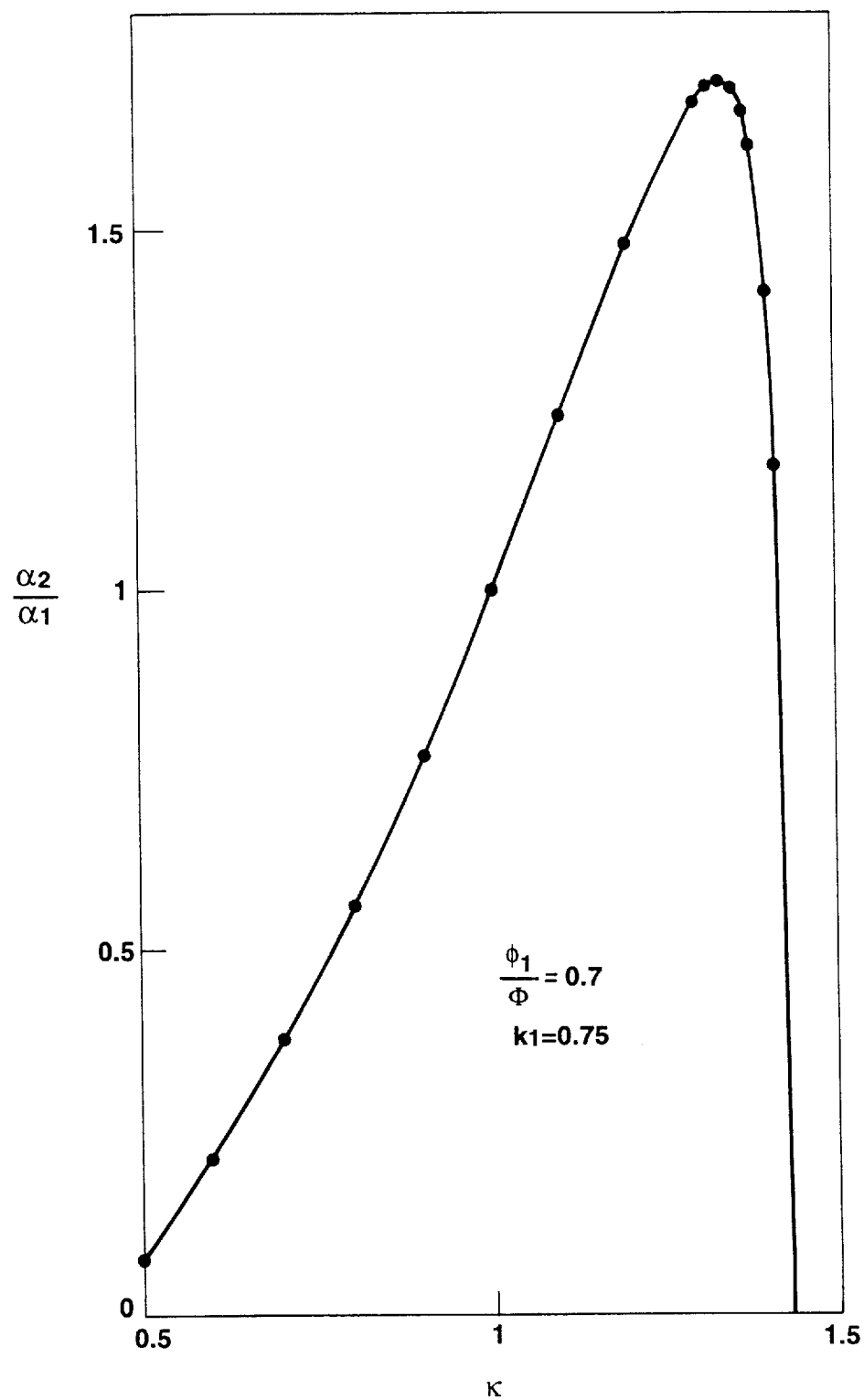

FIG. 5 is a graph plotting the values of the ratio between angles of introversion ($\alpha_2/\alpha_1$). Under the condition that the total brightness is the same, this embodiment ($\kappa > 1$) can provide a larger angle of introversion than the prior art ($\kappa = 1$). In the case of FIG. 5, it is seen that the angle of introversion becomes maximum with a $\kappa$ value ranging from 1.3 to 1.35. When consideration is taken into the thickness of each armor tube which has been ignored in the above calculation, the angle of introversion becomes maximum with a smaller $\kappa$ value ranging from 1 to 1.3. In this embodiment, the occupancy ratio is made larger than 0.7 adopted in the prior art. Thereby, even if the outer diameter of the insertional part is held unchanged, the angle of introversion can be made larger with brightness intact.

The specifications for the stereoscopic-vision endoscope 2 of the first embodiment are listed in Table 2, and data concerning lenses is listed in Table 3 (Table 3-1 lists data concerning lenses included in the objective optical system 18 and relay optical system 20, and Table 3-2 lists data concerning lenses included in the image formation optical system 25). In Table 3 and thereafter, K denotes a surface number, R denotes a radius of curvature, D denotes a spacing between surfaces, N denotes the refractive index of each lens, and ν denotes the Abbe number of each lens.

[TABLE 2]

| Unit | Item | Symbol | First embodiment | Variant | Second embodiment | Third embodiment |
|---|---|---|---|---|---|---|
| Objective optical system | Angle of view | 2ω | 65.1° | 65.1° | 70.2° | 95° |
| | Distance from an object | S | 40 mm | 40 mm | 40 mm | 10 mm |
| | Image height | I' | 3.5 mm | 3.5 mm | 3.5 mm | 1.05 mm |
| | Orientation of a visual field | ... | 0° | 35° | 0° | 0° |
| Relay optical | Outer diameter | φ | 9.2 mm | 9.2 mm | 9.2 mm | 3.1 mm |
| | Numerical aperture | NAr | 0.185 | 0.185 | 0.182 | 0.168 |
| | Squared outer diameter-to-relay length ratio | $\phi^2/L$ | 0.822 | 0.822 | 0.806 | 0.267 |
| | Outer diameter-to-relay length ratio | φ/L | 0.089 | 0.089 | 0.088 | 0.086 |
| | Occupancy ratio | φ/Φ | 0.77 | 0.72 | 0.75 | 0.714 |
| | Focal length-to-relay length ratio | f/L | 0.236 | 0.236 | 0.237 | 0.238 |
| Pupil dividing stop | Dividing ratio | k | 0.75 | 0.75 | 0.75 | 0.75 |
| Whole system | Angle of introversion | α | 2.2° | 2.2° | 2.0° | 1.5° |

TABLE 3-1

(Data concerning lenses included in the objective optical system 18 and relay optical system 20)

| K | R | D | N | ν | |
|---|---|---|---|---|---|
| 1 | ∞ | 0.4 | 1.7682 | 71.79 | |
| 2 | ∞ | 0.2 | | | |
| 3 | ∞ | 0.8 | 1.78472 | 25.76 | |
| 4 | 5.0A | 1.4 | | | |
| 5 | ∞ | 21.57 | 1.883 | 40.78 | |
| 6 | ∞(Entrance pupil) | 5.6 | 1.883 | 40.78 | |
| 7 | −8.314 | 1.1 | | | |
| 8 | −6.259 | 1.0 | 1.57501 | 41.49 | |
| 9 | 9.438 | 3.5 | 1.883 | 40.78 | |
| 10 | −28.64 | 0.7 | | | |
| 11 | ∞ | 11.5 | 1.883 | 40.78 | |
| 12 | −14.132 | 1.3 | | | |
| 13 | −12.955 | 1.7 | 1.80518 | 25.43 | |
| 14 | 5.883 | 5.3 | 1.48749 | 70.21 | |
| 15 | −13.34 | 0.3 | | | |
| 16 | 27.136 | 10.2 | 1.883 | 40.78 | |
| 17 | −13.798 | 1.2 | 1.80518 | 25.43 | |
| 18 | −90.667 | 5.0 | | | |
| 19 | ∞(Image) | 5.0 | | | (←Imege 19) |
| 20 | 18.75 | 34.02 | 1.62004 | 36.25 | |
| 21 | −7.783 | 1.98 | 1.80518 | 25.43 | |
| 22 | −24.364 | 0.5 | | | |
| 23 | 26.158 | 20.0 | 1.62004 | 36.25 | |
| 24 | −26.158 | 0.5 | | | |
| 25 | 24.364 | 1.98 | 1.80518 | 25.43 | |
| 26 | 7.783 | 34.02 | 1.62004 | 36.25 | |
| 27 | −18.75 | 10.0 | | | |
| 28 | 18.75 | 34.02 | 1.62004 | 36.25 | |
| 29 | −7.783 | 1.98 | 1.80518 | 25.43 | |
| 30 | −24.364 | 0.5 | | | |
| 31 | 26.158 | 20.0 | 1.62004 | 36.25 | |
| 32 | −26.258 | 0.5 | | | |
| 33 | 24.364 | 1.98 | 1.80518 | 25.43 | |
| 34 | 7.783 | 34.02 | 1.62004 | 36.25 | |
| 35 | −18.75 | 10.0 | | | |
| 36 | 18.75 | 34.02 | 1.62004 | 36.25 | |
| 37 | −7.783 | 1.98 | 1.80518 | 25.43 | |
| 38 | −24.364 | 0.5 | | | |
| 39 | 26.158 | 20.0 | 1.62004 | 36.25 | |
| 40 | −26.158 | 0.5 | | | |
| 41 | 19.375 | 3.0 | 1.883 | 40.78 | |
| 42 | ∞ | 1.5 | 1.72825 | 28.46 | |
| 43 | 8.682 | 6.12 | | | |
| 44 | 12.42 | 3.0 | 1.7725 | 49.6 | |
| 45 | 19.072 | 20.78 | | | |
| 46 | 16.619 | 4.0 | 1.883 | 40.78 | |
| 47 | 135.138 | 6.0 | | | |
| 48 | ∞ | | | | (←Image 21) |

TABLE 3-2

(Data concerning lenses included in the image formation optical system 25)

| K | R | D | N | ν | |
|---|---|---|---|---|---|
| 1 | ∞ | 25.3 | | | (←Image 21) |
| 2 | ∞ | 3.0 | 1.7682 | 71.79 | |
| 3 | ∞ | 5.0 | | | |
| 4 | ∞(Stop) | 10.0 | | | |
| 5 | ∞ | 1.0 | 1.51633 | 64.15 | |
| 6 | ∞ | 2.0 | | | |
| 7 | −75.495 | 1.5 | 1.78472 | 25.71 | |
| 8 | 18.75 | 9.71 | 1.7725 | 49.6 | |
| 9 | −27.981 | 5.0 | | | |
| 10 | 45.284 | 4.0 | 1.7725 | 49.6 | |
| 11 | −45.284 | 12.97 | | | |
| 12 | −19.179 | 1.5 | 1.6668 | 33.04 | |
| 13 | −112.735 | | | | |

The angle of introversion is determined with the spacing between the centers of gravity of the entrance pupils 47a and 47b and the distance from an object. That is to say, the angle of introversion is determined according to the expression (3), whereas the distance from an object S and the angle of view ω are ratings dependent on a purpose of use and do not substantially contribute to the increase of the angle of introversion. Larger pupil dividing ratios k result in larger angles of introversion. The larger the k value is, the smaller the apertures of the pupil dividing stop become. The amount of light diminishes. Consequently, the imaging means fail to achieve image pickup. In practice, therefore, the pupil dividing ratio k is limited. When the ratio n of an image height is made too small, the amount of perimetric light decreases. The ratio of an image height is therefore set to the range from 0.35 to 0.4. When the ratio m of a focal length to a relay length is made too small, the amount of transmitted light decreases. The ratio of a focal length to a relay length should preferably range from 0.2 to 0.3. For increasing the angle of introversion, the quotient of $\phi^2/L$ should be made larger.

For the first and second conventional endoscopes, the value of the ratio of a squared outer diameter to a relay length L ($\phi^2/L$) is about 0.42. In this embodiment, the value is set to 0.43 or larger. Although the angle of view is larger than those in the conventional endoscopes, the angle of introversion is as large as 2°. Consequently, a necessary sense of three-dimensionality can be provided.

As for the usage of an endoscope, commonly, a large-diameter endoscope is used to observe a space permitting a large distance from an object, and a small-diameter endoscope is used to observe a zone permitting a small distance from an object. The distance from an object, S, and the outer diameter, $\phi$, of a relay optical system, which are ratings, correlate with each other. The quotient of $\phi/S$ ranges from 0.15 to 0.3. Assuming that a constant is specified as the quotient of $\phi/S$ in the expression (3), the quotient of $\phi/L$ should be made larger in order to increase the angle of introversion. In the first and second conventional endoscopes, the quotient of $\phi/L$ is about 0.06. In this embodiment, the quotient of $\phi/L$ is set to 0.07 or larger. The endoscope of this embodiment can therefore provide a larger angle of introversion than the conventional endoscopes.

When the outer diameter Φ of the insertional part is made larger, the outer diameter $\phi$ of a relay optical system can be increased. For alleviating patient discomfort, the outer diameter Φ of the insertional part should be as small as possible. In the insertional part, light guides for guiding illumination light are placed in parallel with one another in addition to the observation optical system. For a conventional stereoscopic-vision endoscope, the value of the (occupancy) ratio of the outer diameter $\phi$ of a relay optical system to the outer diameter Φ of the insertional part ($\phi/\Phi$) is about 0.7. As described in conjunction with FIGS. 3 to 5, the value is set to 0.71 or larger in this embodiment. Thus, an intense sense of three-dimensionality is provided despite the minimized outer diameter. More preferably, the value should be 0.72 or larger. Thus, the effect of providing an intense sense of three-dimensionality despite the minimized outer diameter can be exerted fully.

Figure 6:
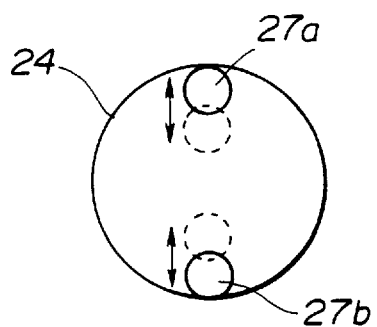
Figure 7:
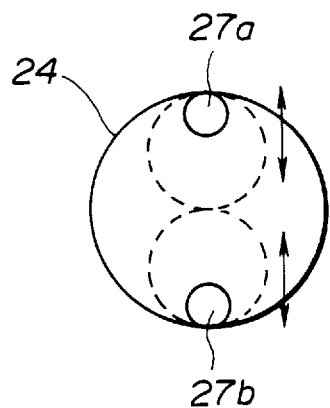

An endoscope may be designed to provide an optimal sense of three-dimensionality in consideration of operator's likes or an employed technique. In this case, the spacing between the two apertures 27a and 27b of the pupil dividing stop 24 is made variable so that the angle of introversion can be varied. For realizing a compact design, as shown in FIG. 6, the two apertures 27a and 27b may be made movable in mutually opposite directions perpendicular to the optical axis of the relay optical system 20 so that the spacing between them will be variable. As shown in FIG. 7, when the two apertures 27a and 27b are brought closer so that the diameters thereof will be larger, brightness can be upgraded. The structure of the pupil dividing stop 24 may be any of those shown in FIGS. 8 to 10. Alternatively, an electro-optic device such as a liquid-crystal optical device may be employed.

Figure 8:
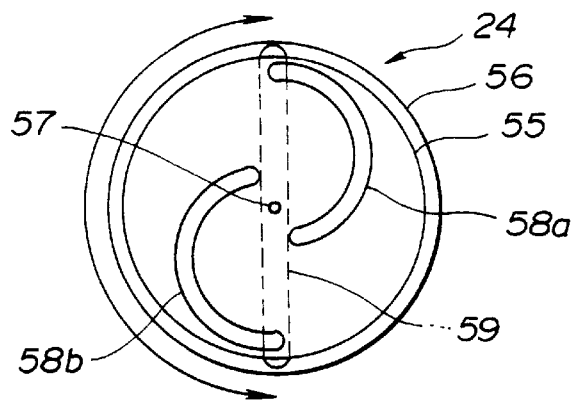
Figure 9:
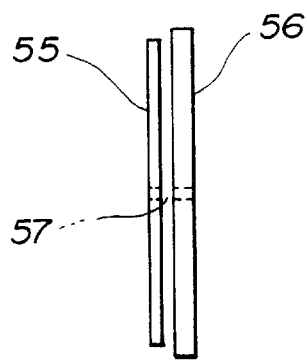

A pupil dividing stop shown in FIG. 8 is composed of two plate-like stops 55 and 56 which can rotate about an axis 57 (FIG. 9 is a side view of FIG. 8). The stop 55 has spiral apertures 58a and 58b, and the stop 56 has a linear aperture 59. Only the portions of the apertures in the two stops 55 and 56 coinciding with each other pass light. The positions of the mutually-coinciding portions of the apertures can be changed by turning the stops.

Figure 10:
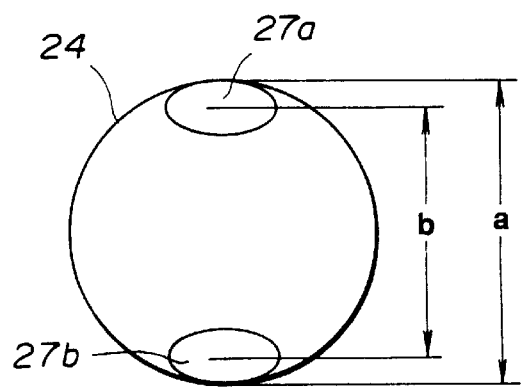

When the dividing ratio k is made larger, the angle of introversion increases and the pupil dividing stop 24 has a small aperture. This leads to lowered brightness. However, as shown in FIG. 10, when apertures 27a and 27b are shaped so that the diameters of the apertures along the circumference of the pupil dividing stop 24 will be larger than those in the direction of the radius of the pupil dividing stop 24, the apertures enjoy a large area and brightness rises. In this case, b in the expression providing the dividing ratio, k=b/a, denotes the spacing between the centers of gravity of the apertures 27a and 27b.

Figure 11:
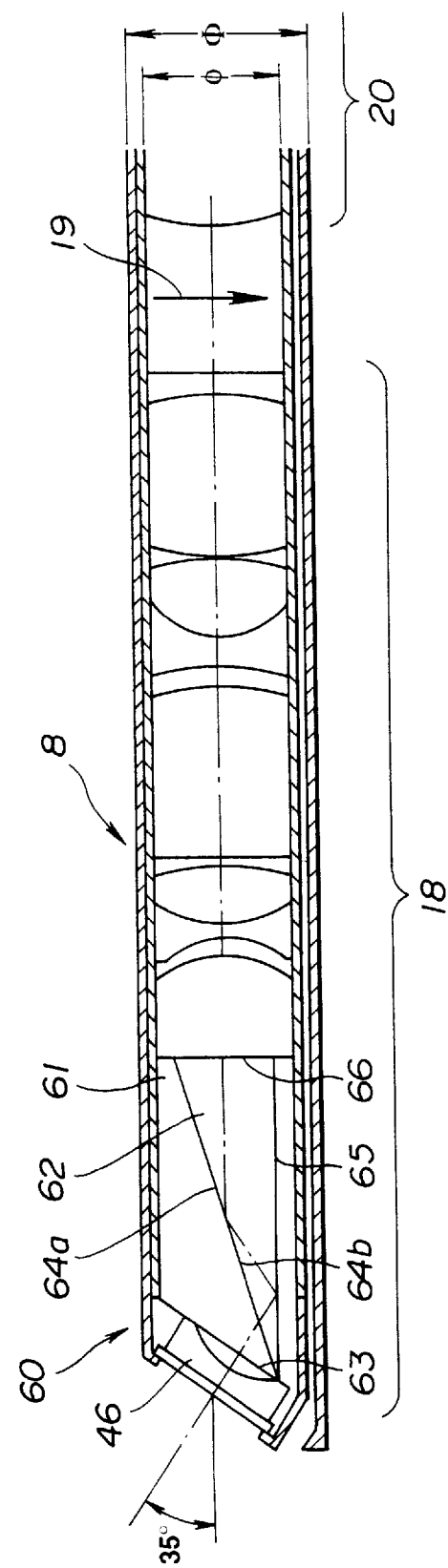

FIG. 11 shows a variant of an imaging optical system in the stereoscopic-vision endoscope of the first embodiment. The thick parallel planes of the fifth and sixth surfaces of the first embodiment shown in FIG. 2 are replaced with a skew-vision prism 60 that provides a light path having the same length as the one provided by the fifth and sixth surfaces.

The skew-vision prism 60 consists of a first prism 61 and a second prism 62 which are arranged in that order starting from the outermost object space. The first prism 61 has a first surface 63 and a second surface 64a, while the second prism 62 has a first surface 64b, a second surface 65, and a third surface 66. The second surface 65 of the second prism 62 is substantially parallel with the optical axis of the relay optical system 20. The first surface 64a of the first prism 61 is attached to the first surface 64b of the second prism 62 using an adhesive. Light emanating from an object passes through the first surface 63 of the first prism 61 and comes out of the second surface 64a. Thereafter, the light is irradiated to the first surface 64b of the second prism 62, reflected totally from the second surface 65 and first surface 64b in that order, and then emitted from the third surface 66. In this variant, the orientation of a visual field is 35°.

The light beam entering the first surface 64b of the second prism 62 from the second surface 64a of the first prism 61 through the adhesive has a small angle of incidence with respect to each surface and is not reflected totally. By contrast, the light beam traveling from the second surface 65 of the second prism 62 to the first surface 64b has a large angle of incidence relative to the first surface 64b and is reflected totally due to the difference in refractive index between the glass and adhesive. Incidentally, the refractive index of the adhesive is smaller than that of the glass.

For the skew-vision objective optical system shown in FIG. 11, a distal concave lens is placed askew with respect to the longitudinal direction of the insertional part so that the optical axis of the distal concave lens will align with the orientation of a visual field. The distal concave lens must have a smaller outer diameter than the other lenses in the objective optical system or relay lenses, so that the distal concave lens can be mounted in an armor tube of the insertional part 8.

Since one of the surfaces of the aspheric lens 46 is formed as a flat plane, degradation in image quality due to an error or deviation in position of an optical axis between the surfaces does not occur. The application of an aspheric lens is not limited to the objective optical system but may be used for any other optical system.

In FIG. 11, the value of the ratio of the outer diameter φ of an objective optical system or relay optical system to the outer diameter Φ of an insertional part is 0.72. The value is about 0.7 for a conventional stereoscopic-vision endoscope having light guides. According to the present invention, while the outer diameter of an endoscope is the same as that of the conventional endoscope, the diameter of a relay optical system can be made larger and the sense of three-dimensionality can be intensified. For emphasizing this effect, the value of the ratio should range from 0.75 to 0.85. With this value, a maximum sense of three-dimensionality can be provided with an appropriate amount of illumination light maintained. When the occupancy ratio of the relay optical system is made larger, the occupancy ratio of light guides decreases relatively. The amount of transmitted illumination light diminishes accordingly. These decreases can be compensated for by raising the brightness of an observation optical system, increasing the numerical aperture in the light guides, or intensifying the luminance of a light source. Alternatively, the decreases can be compensated for by employing high-sensitivity imaging devices.

Next, the second embodiment will be described.

Figure 12:
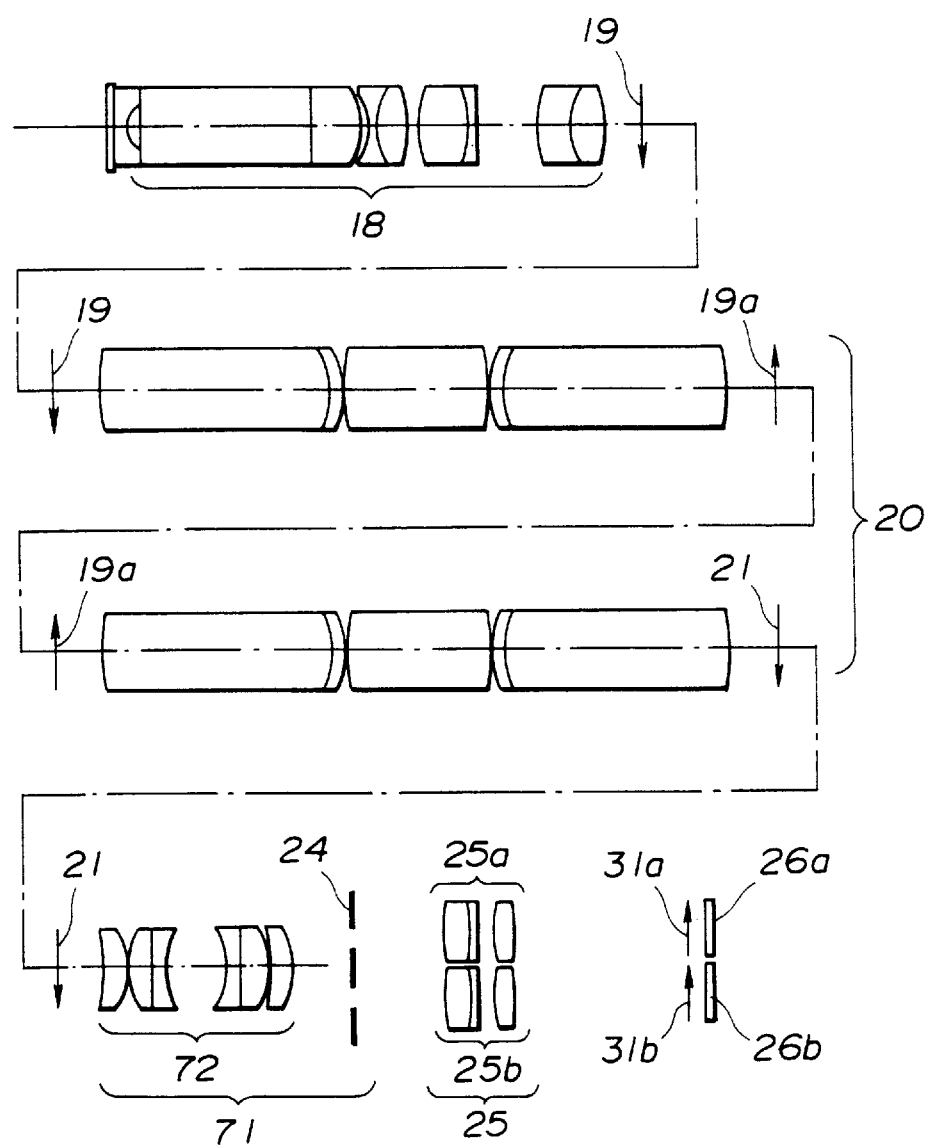
FIG. 12 shows the components of an imaging optical system in a stereoscopic-vision endoscope in accordance with the second embodiment of the present invention.

FIG. 12 shows an imaging optical system for a stereoscopic-vision endoscope of the second embodiment of the present invention. The imaging optical system comprises an objective optical system 18, a relay optical system 20, a pupil dividing means 71, an image formation optical system 25, and imaging devices 26a and 26b which are arranged in that order starting from the outermost object space. The pupil dividing means 71 is composed of a pupil formation optical system 72 and a pupil dividing stop 24. The pupil formation optical system 72 receives a light beam emanating from a final image 21 formed by the relay optical system and converges the light beam to infinity.

The other components are identical to those of the first embodiment.

An embodiment described in Germany Utility Model Unexamined Publication No. G9217980.0 or G9302898.2 has been proposed as a stereoscopic-vision endoscope of the aforesaid type. A pupil formation optical system described in the publication is realized with one juncture lens. However, when a bright optical system permitting a large numerical aperture and a compact grip similar to those in this embodiment are needed, the known simple structure of one juncture lens fails to correct aberration. This results in deteriorated image quality.

In this embodiment, a pupil formation optical system composed of two or more groups of lenses including a juncture lens, which is shown in FIG. 12, is employed. The operation and effect are identical to those of the first embodiment.

The specifications for the second embodiment are identical to those for the first embodiment listed in Table 2. Data concerning lenses are listed in Table 4 below.

TABLE 4

| K | R | D | N | ν |
|---|---|---|---|---|
| 1 | ∞ | 1.0 | 1.51633 | 64.1 |
| 2 | ∞ | 0.3 | | |
| 3 | ∞ | 1.5 | 1.72916 | 54.7 |
| 4 | 4.456 | 2.5 | | |
| 5 | ∞ | 22.02 | 1.883 | 40.8 |
| 6 | ∞ | 5.39 | 1.883 | 40.8 |
| 7 | −10.399 | 1.02 | | |
| 8 | −8.619 | 2.0 | 1.62004 | 36.3 |
| 9 | ∞ | 3.5 | 1.788 | 47.4 |

TABLE 4-continued

| K | R | D | N | ν |
|---|---|---|---|---|
| 10 | −14.168 | 2.28 | | |
| 11 | 24.181 | 6.14 | | |
| 12 | −11.747 | 3.0 | 1.78472 | 25.7 |
| 13 | ∞ | 8.65 | | |
| 14 | 38.289 | 3.0 | 1.59551 | 39.2 |
| 15 | 11.422 | 6.0 | 1.51633 | 64.1 |
| 16 | −19.272 | 10.0 | | |
| 17 | 17.756 | 32.5 | 1.51633 | 64.1 |
| 18 | −9.403 | 1.5 | 1.801 | 35.0 |
| 19 | −18.636 | 0.5 | | |
| 20 | 36.09 | 2.0 | 1.72916 | 54.7 |
| 21 | ∞ | 22.0 | 1.51633 | 64.1 |
| 22 | ∞ | 2.0 | 1.72916 | 54.7 |
| 23 | −36.09 | 0.5 | | |
| 24 | 18.636 | 1.5 | 1.801 | 35.0 |
| 25 | 9.403 | 32.5 | 1.51633 | 64.1 |
| 26 | −17.756 | 10.0 | | |
| 27 | 17.756 | 32.5 | 1.51633 | 64.1 |
| 28 | −9.403 | 1.5 | 1.801 | 35.0 |
| 29 | −18.636 | 0.5 | | |
| 30 | 36.09 | 2.0 | 1.72916 | 54.7 |
| 31 | ∞ | 22.0 | 1.51633 | 64.1 |
| 32 | ∞ | 2.0 | 1.72916 | 54.7 |
| 33 | −36.09 | 0.5 | | |
| 34 | 18.636 | 1.5 | 1.801 | 35.0 |
| 35 | 9.403 | 32.5 | 1.51633 | 64.1 |
| 36 | −17.756 | 20.95 | | |
| 37 | 51.24 | 4.9 | 1.72916 | 54.7 |
| 38 | −30.808 | 0.35 | | |
| 39 | 15.166 | 4.93 | 1.617 | 62.8 |
| 40 | 47.26 | 1.65 | 1.5927 | 35.3 |
| 41 | 10.61 | 7.0 | | |
| 42 | −8.871 | 2.07 | 1.7552 | 27.5 |
| 43 | −42.795 | 7.38 | 1.6968 | 56.5 |
| 44 | −13.948 | 0.48 | | |
| 45 | ∞ | 4.7 | 1.804 | 46.6 |
| 46 | −45.751 | 8.66 | | |
| 47 | ∞ | 31.26 | | |
| 48 | 47.104 | 3.5 | 1.51633 | 64.1 |
| 49 | −22.015 | 1.5 | 1.78472 | 25.7 |
| 50 | −48.137 | 1.0 | | |
| 51 | 79.158 | 3.0 | 1.5725 | 57.8 |
| 52 | −79.158 | 32.174 | | |
| 53 | ∞ | | | |

Next, the third embodiment will be described.

Figure 13:
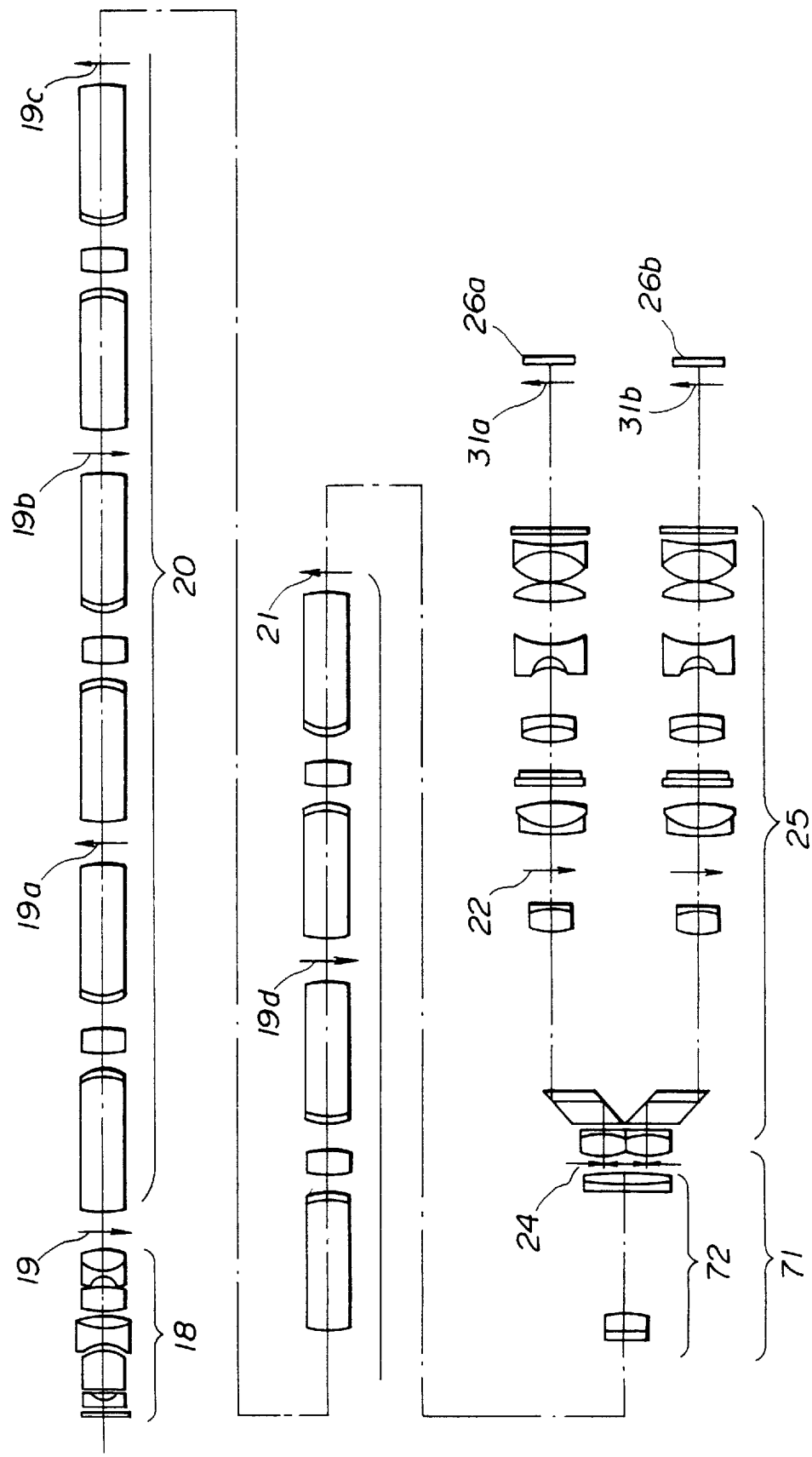
FIG. 13 shows the components of an imaging optical system in a stereoscopic-vision endoscope in accordance with the third embodiment of the present invention.

FIG. 13 shows an imaging optical system for a stereoscopic-vision endoscope of the third embodiment of the present invention. The imaging optical system comprises an objective optical system 18, a relay optical system 20, a pupil dividing means 71, an image formation optical system 25, and imaging devices 26a and 26b which are arranged in that order starting from the outermost object space. The pupil dividing means 71 is composed of a pupil formation optical system 72 and a pupil dividing stop 24. The image formation optical system 72 receives a light beam emanating from a final image 21 formed by the relay optical system and converges the light beam to infinity.

The other components are identical to those of the first embodiment.

In the third embodiment, the outer diameter of the relay optical system 20 is as small as 3.1 mm. The outer diameter of the insertional part is smaller than that in any of the other embodiments. The number of relays made in the relay optical system 20 is five. This means that the insertional part has a sufficient length. The angle of view is 95° or wider than that in any of the other embodiments or prior arts. This small-diameter stereoscopic-vision endoscope is used for treatment in a limited space in the brain or joint. Under the conditions of a distance from an object rated in the specifications, a small outer diameter of an insertional part, and a wide angle of view, this embodiment ensures a necessary and sufficient sense of three-dimensionality (angle of introversion). The other operations and effects are identical to those of the first embodiment.

The specifications for the third embodiment are identical to those for the first embodiment listed in Table 2. Data concerning lenses are set forth in Tables 5 and 6 below.

TABLE 5

| K | R | D | N | ν | |
|---|---|---|---|---|---|
| 1 | ∞ | 0.3 | 1.51633 | 64.15 | |
| 2 | ∞ | 0.1 | | | |
| 3 | ∞ | 0.2 | 1.64769 | 33.80 | |
| 4 | 0.6637 | 0.3 | | | |
| 5 | ∞ | 3.1135 | 1.883 | 40.78 | |
| 6 | −1.6884 | 0.3 | | | |
| 7 | −1.8348 | 0.4 | 1.59551 | 39.21 | |
| 8 | 3.6295 | 1.0 | 1.788 | 47.38 | |
| 9 | −5.0327 | 0.2 | | | |
| 10 | 3.4858 | 1.7 | 1.7725 | 49.60 | |
| 11 | −6.4317 | 0.5 | | | |
| 12 | −1.7123 | 0.45 | 1.80518 | 25.43 | |
| 13 | ∞ | 1.3 | 1.51633 | 64.15 | |
| 14 | −1.993 | 1.5 | | | (The above data items are concerned with the objective optical system) |
| 15 | ∞ | 2.7 | | | (←Image 19) |
| 16 | 8.3956 | 9.6653 | 1.7725 | 49.6 | |
| 17 | −2.2510 | 1.0 | 1.834 | 37.17 | |
| 18 | −11.2786 | 3.1347 | | | |
| 19 | 16.6510 | 3.0 | 1.7725 | 49.6 | |
| 20 | −16.6510 | 3.1347 | | | |
| 21 | 11.2786 | 1.0 | 1.834 | 37.17 | |
| 22 | 2.510 | 9.6653 | 1.7725 | 49.6 | |
| 23 | −8.3956 | 2.7 | | | |
| 24 | ∞ | 2.7 | | | (←Image 19a) |
| 25 | −8.3956 | 9.6653 | 1.7725 | 49.6 | |
| 26 | −2.2510 | 1.0 | 1.834 | 37.17 | |
| 27 | 11.2786 | 3.1347 | | | |
| 28 | 16.6510 | 3.0 | 1.7725 | 49.6 | |
| 29 | −16.6510 | 3.1347 | | | |
| 30 | 11.2786 | 1.0 | 1.834 | 37.17 | |
| 31 | 2.510 | 9.6653 | 1.7725 | 49.6 | |
| 32 | −8.3956 | 2.7 | | | |
| 33 | ∞ | 2.7 | | | (←Image 19b) |
| 34 | 8.3956 | 9.6653 | 1.7725 | 49.6 | |
| 35 | −2.2510 | 1.0 | 1.834 | 37.17 | |
| 36 | −11.2786 | 3.1347 | | | |
| 37 | 16.6510 | 3.0 | 1.7725 | 49.6 | |
| 38 | −16.6510 | 3.1347 | | | |
| 39 | 11.2786 | 1.0 | 1.834 | 37.17 | |
| 40 | 2.510 | 9.6653 | 1.7725 | 49.6 | |
| 41 | −8.3956 | 2.7 | | | |
| 42 | ∞ | 2.7 | | | (←Image 19c) |
| 43 | 8.3956 | 9.6653 | 1.7725 | 49.6 | |
| 44 | −2.2510 | 1.0 | 1.834 | 37.17 | |
| 45 | −11.2786 | 3.1347 | | | |
| 46 | 16.6510 | 3.0 | 1.7725 | 49.6 | |
| 47 | −16.6510 | 3.1347 | | | |
| 48 | 11.2786 | 1.0 | 1.834 | 37.17 | |
| 49 | 2.510 | 9.6653 | 1.7725 | 49.6 | |
| 50 | 8.3956 | 2.7 | | | |
| 51 | ∞ | 2.7 | | | (←Image 19d) |
| 52 | 8.3956 | 9.6653 | 1.7725 | 49.6 | |
| 53 | −2.2510 | 1.0 | 1.834 | 37.17 | |
| 54 | −11.2786 | 3.1347 | | | |
| 55 | 16.6510 | 3.0 | 1.7725 | 49.6 | |
| 56 | −16.6510 | 3.1347 | | | |
| 57 | 11.2786 | 1.0 | 1.834 | 37.17 | |
| 58 | 2.510 | 9.6653 | 1.7725 | 49.6 | |
| 59 | −8.3956 | 2.7 | | | |
| 60 | ∞ | | | | (The above data is concerned with the relay optical system) |

TABLE 6

| K | R | D | N | v | |
|---|---|---|---|---|---|
| 1 | ∞ | 5.9557 | | | (←Image 21) |
| 2 | −30.7373 | 1.0 | 1.84666 | 23.78 | |
| 3 | 31.1886 | 3.0 | 1.51633 | 64.15 | |
| 4 | −8.0907 | 29.4142 | | | |
| 5 | 781.9691 | 1.5 | 1.801 | 34.97 | |
| 6 | 27.5115 | 3.0 | 1.6516 | 58.52 | |
| 7 | −23.5275 | 2.0 | | | (The above data is concerned with the pupil formation optical system) |
| 8 | ∞ | 2.0 | | | (←Pupil dividing stop) |
| 9 | 35.0928 | 2.1 | 1.57099 | 50.8 | |
| 10 | −23.8555 | 1.1 | 1.71736 | 29.51 | |
| 11 | −83.9153 | 2.5 | | | |
| 12 | ∞ | 14.65 | 1.8061 | 40.95 | (←Prism) |
| 13 | ∞ | 25.1325 | | | |
| 14 | 19.6977 | 2.8 | 1.6968 | 55.53 | |
| 15 | −15.8987 | 1.0 | 1.76182 | 26.52 | |
| 16 | 1274.6855 | 8.6 | | | |
| 17 | ∞ | 16.25 | | | (←Image 22) |
| 18 | 21.218 | 0.9 | 1.78472 | 25.71 | |
| 19 | 8.175 | 2.6 | 1.66672 | 48.32 | |
| 20 | −18.796 | 2.0 | | | |
| 21 | ∞ | 1.0 | 1.51633 | 64.15 | |
| 22 | ∞ | 0.5 | | | |
| 23 | ∞ | 1.0 | 1.51633 | 64.15 | |
| 24 | ∞ | 3.1 | | | |
| 25 | 13.710 | 1.37 | 1.71999 | 50.25 | |
| 26 | −13.710 | 1.0 | 1.78472 | 25.71 | |
| 27 | ∞ | 6.71 | | | |
| 28 | −6.812 | 1.5 | 1.84666 | 23.78 | |
| 29 | −3.705 | 0.8 | 1.62374 | 47.05 | |
| 30 | 8.719 | 4.526 | | | |
| 31 | 18.929 | 2.76 | 1.62041 | 60.26 | |
| 32 | −13.442 | 0.2 | | | |
| 33 | 9.197 | 4.71 | 1.51633 | 64.15 | |
| 34 | −9.197 | 0.8 | 1.85026 | 32.29 | |
| 35 | 23.081 | 3.596 | | | |
| 36 | ∞ | 1.0 | 1.51633 | 64.15 | |
| 37 | ∞ | | | | (The above data is concerned with the image formation optical system) | image. The m value permitting an optimal amount of light is calculated as described below.

Japanese Patent Laid-Open No. 4-93909 describes power assignment and optimization of an amount of transmitted light for a system of relay lenses of a Hopkins type. A composite focal length f provided by thin lenses L1 and L2 shown in FIG. 1 furnished in the unexamined publication is calculated according to the expressions below.

$$\frac{1}{f} = \frac{1}{f_1} + \frac{1}{f_2} - \frac{d_2/n}{f_1 \cdot f_2}$$

$$f_1 = \frac{(d_2/n)(d_2/n + 2d_1) \pm (d_2/n)\sqrt{(d_2/n)^2 + 4d_1 d_3}}{2(d_2/n - d_3 + d_1)}$$

$$f_2 = \frac{d_3(f_1 - d_2/n)}{(f_1 - d_2/n) - d_3}$$

$$d_2 = L - (d_1 + d_3)$$

Using the conditional expressions (conditional expressions (4) and (5) in the above unexamined publication) below for imposing conditions for eliminating vignetting in the perimeter of a visual field and for increasing an amount of transmitted light, the ratio, m, of a focal length to a relay length is calculated as per Table 5.

Conditional expressions:

$0.3 > d_1/(L/2) > 0.1$ $0.2 > d_3/(L/2) \geq 0$

Table 7 demonstrates that for optimization of the amount of light transmitted by the system of relay lenses of the Hopkins type, the ratio, m, of a focal length to a relay length is set to the range from 0.2 to 0.3. When the m value is smaller than 0.2 or larger than 0.3, the amount of transmitted light decreases. This is undesirable because a dark image is produced and vignetting occurs in the perimeter of an image.

TABLE 7

| $d_3/(L/2)$ | | 0.05 | | | 0.1 | | | 0.2 | | |
|---|---|---|---|---|---|---|---|---|---|---|
| $d_1/(L/2)$ | n | 0.5 | 1.6 | 1.7 | 1.5 | 1.6 | 1.7 | 1.5 | 1.6 | 1.7 |
| 0.1 | | 0.29 | 0.27 | 0.26 | 0.28 | 0.26 | 0.25 | 0.25 | 0.24 | 0.23 |
| 0.2 | | 0.26 | 0.24 | 0.23 | 0.25 | 0.24 | 0.23 | 0.24 | 0.23 | 0.22 |
| 0.3 | | 0.23 | 0.22 | 0.21 | 0.23 | 0.22 | 0.21 | 0.23 | 0.22 | 0.22 |

In the aforesaid first to third embodiments, the ratio, m (=f/L), of a focal length to a relay length in one system of relay lenses is smaller than those in the aforesaid prior arts. Compared with a large ratio of a focal length to a relay length, a small ratio may lead to the larger NAr value or the larger numerical aperture permitted by the relay optical system as long as the outer diameter φ is the same. When the ratio, m, of a focal distance to a relay length is too small, the amount of transmitted light decreases to produce a darker The m value in the above unexamined publication is about 0.3. By making the m value closer to 0.2, the numerical aperture permitted by a relay optical system can be increased and an angle of introversion can be widened.

Figure 14:
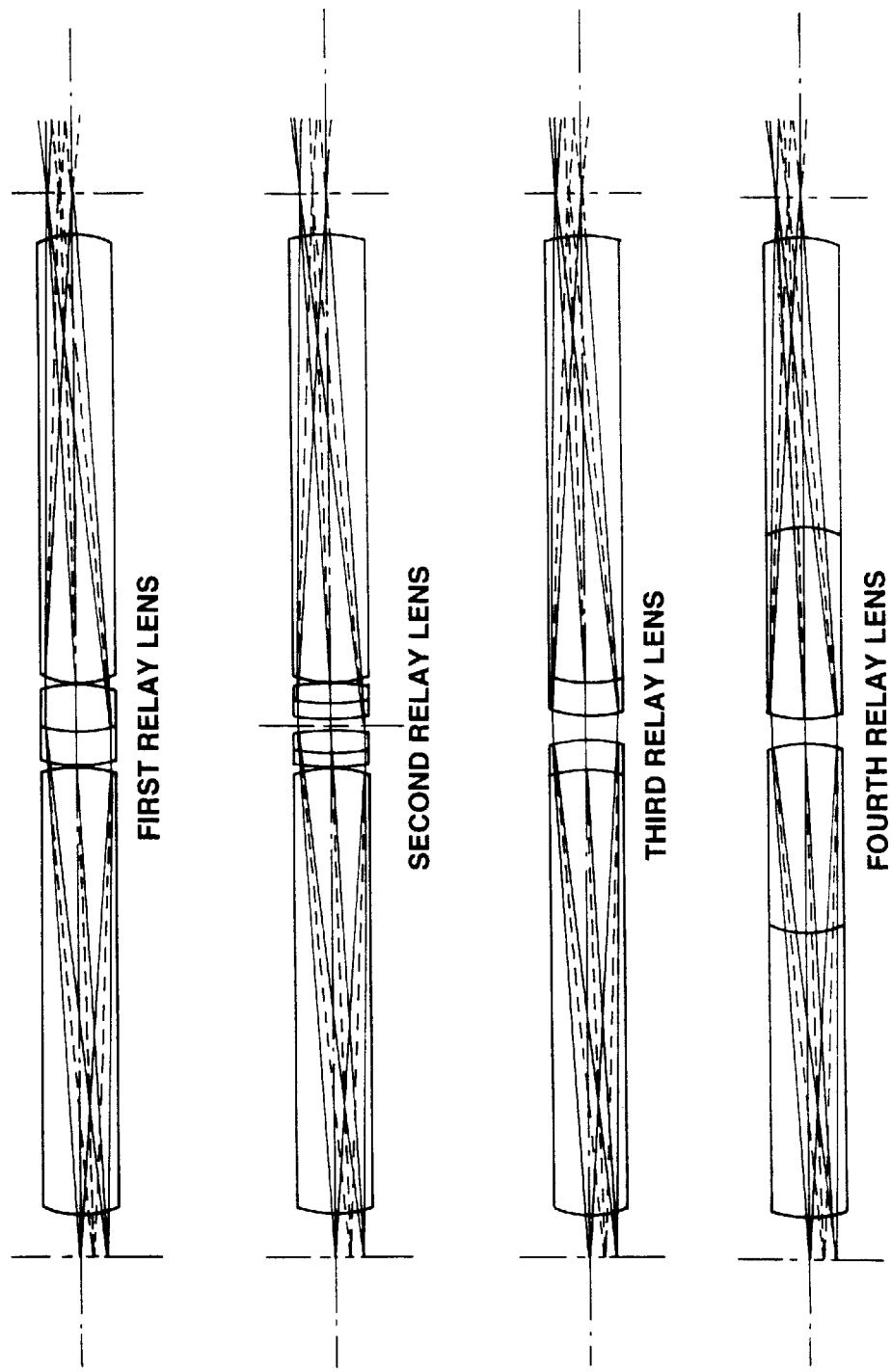
FIG. 14 shows the components of a relay optical system adaptable to the embodiments of the present invention.
Figure 15:
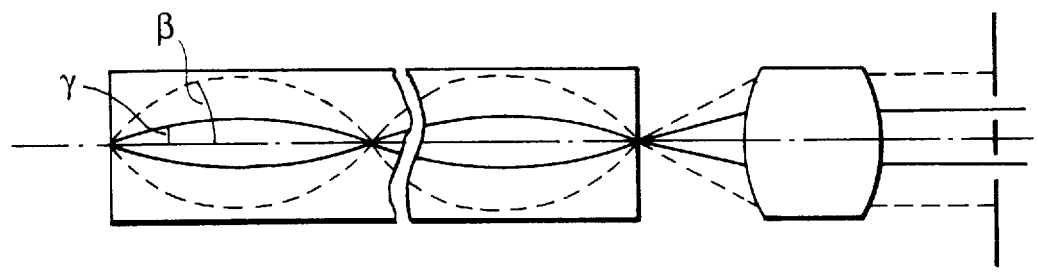
FIGS. 15 to 28 are explanatory diagrams concerning the numerical apertures $NA_R$ and NAr permitted by a refractive index distribution type lens in accordance with the fourth embodiment of the present invention.

FIG. 14 shows another relay optical systems adaptable to the first and second embodiments.

Table 8 lists the specifications for each system of relay lenses shown in FIG. 14, and Tables 9 to 12 list data concerning the lenses.

[TABLE 8]

| Item | Symbol | First relay lens | Second relay lens | Third relay lens | Fourth relay lens |
|---|---|---|---|---|---|
| Outer diameter | φ | 9.2 mm | 8.8 mm | 4.6 mm | 6 mm |
| Image height | I' | 3.5 mm | 3 mm | 1.8 mm | 2.3 mm |
| Numerical aperture | NAr | 0.133 | 0.142 | 0.173 | 0.156 |
| Squared outer diameter-to-relay length ratio | φ²/L | 0.618 | 0.685 | 0.45 | 0.573 |
| Outer diameter-to-relay length ratio | φ/L | 0.067 | 0.078 | 0.098 | 0.095 |
| Occupancy ratio | φ/Φ | 0.72 | 0.75 | 0.8 | 0.77 |
| Focal length-to-relay length ratio | f/L | 0.248 | 0.274 | 0.284 | 0.307 |

TABLE 9

(Data concerning lenses included in the first relay lens in FIG. 14)

| K | R | D | N | ν |
|---|---|---|---|---|
| 1 | ∞ | 4.0 | | |
| 2 | 26.4959 | 57.0 | 1.6968 | 55.53 |
| 3 | −52.6793 | 1.0 | | |
| 4 | 44.2526 | 4.0 | 1.80518 | 25.43 |
| 5 | 17.7268 | 6.0 | 1.6516 | 58.52 |
| 6 | −40.4198 | 1.0 | | |
| 7 | 52.6793 | 57.0 | 1.6968 | 55.53 |
| 8 | −26.4959 | 4.0 | | |
| 9 | ∞ | | | |

TABLE 10

(Data concerning lenses included in the second relay lens in FIG. 14)

| K | R | D | N | ν |
|---|---|---|---|---|
| 1 | ∞ | 4.0 | | |
| 2 | 21.1895 | 43.7 | 1.62004 | 36.25 |
| 3 | −834.4062 | 2.0 | | |
| 4 | 32.2884 | 1.57 | 1.8061 | 40.95 |
| 5 | 14.563 | 3.93 | 1.60311 | 60.7 |
| 6 | −34.7147 | 1.3 | | |
| 7 | ∞ | 1.3 | | |
| 8 | 34.7147 | 3.93 | 1.60311 | 60.7 |
| 9 | −14.563 | 1.57 | 1.8061 | 40.95 |
| 10 | −32.2884 | 2.0 | | |
| 11 | 834.4062 | 43.7 | 1.62004 | 36.25 |
| 12 | −21.1895 | 4.0 | | |
| 13 | ∞ | | | |

TABLE 11

(Data concerning lenses included in the third relay lens in FIG. 14)

| K | R | D | N | ν |
|---|---|---|---|---|
| 1 | ∞ | 2.0 | | |
| 2 | 8.4956 | 19.34 | 1.58913 | 61.18 |
| 3 | −3.8709 | 1.16 | 1.72342 | 37.95 |
| 4 | −7.4633 | 2.0 | | |
| 5 | 7.4633 | 1.16 | 1.72342 | 37.95 |
| 6 | 3.8709 | 19.34 | 1.58913 | 61.18 |
| 7 | −8.4956 | 2.0 | | |
| 8 | ∞ | | | |

TABLE 12

(Data concerning lenses included in the fourth relay lens in FIG. 14)

| K | R | D | N | ν |
|---|---|---|---|---|
| 1 | ∞ | 2.0 | | |
| 2 | 11.9575 | 15.0 | 1.801 | 34.97 |
| 3 | 4.767 | 13.36 | 1.618 | 63.39 |
| 4 | −9.7709 | 2.1 | | |
| 5 | 9.7709 | 13.36 | 1.618 | 63.39 |
| 6 | −4.767 | 15.0 | 1.801 | 34.97 |
| 7 | −11.9575 | 2.0 | | |
| 8 | ∞ | | | |

In the first to third embodiments, various kinds of solid-state imaging devices (what are generally known in the name of a CCD, PCD, CMD, AMI, and SIT) or image pickup tubes (what are generally known in the name of Saticon, Vidicon, and HARP) may be used as the imaging devices 26a and 26b.

An image intensifier or the like may be used to improve sensitivity.

The imaging devices 26a and 26b may be of a single plate type and used for color imaging or may be designed as a dual- or triple-plate type camera for color imaging.

In FIG. 1, a simultaneous illumination and imaging technique is adopted, wherein the imaging devices 26a and 26b in each of which a color-separation filter such as a mosaic filter is incorporated are used to achieve color imaging under illumination of white light. The present invention is not limited to the simultaneous technique but may apply to a field sequential imaging technique for color imaging in which the imaging devices 26a and 26 each having no color-separation filter pick up three primary color components so as to form an image during field sequential illumination during which illumination light having the wavelengths of red, green, and blue is emitted sequentially to an object.

Next, the fourth embodiment will be described. Prior to particular description, mention will be made of the concept of the fourth embodiment.

A stereoscopic-vision endoscope of the fourth embodiment comprises: an insertional part to be inserted into a body cavity of a living body or any other object; an image formation optical system that uses a pupil dividing means to divide a light beam emanating from an object image formed by an optical system, which lies in the insertional part, has one optical axis, and contains at least one relay lens, into a plurality of portions substantially at a position of entrance-image formation, and then forms at least two object images having parallax; and imaging means for picking up the object images formed by the image formation optical system. The stereoscopic-vision endoscope enables stereoscopic observation. Assuming that the numerical aperture determined with the effective diameter of a relay lens is $NA_R$, and the numerical aperture in a relay lens, which is determined with a ray traveling as the center of each light beam at the position of division made by the pupil dividing means, is NAr, the condition (B1) below is satisfied. Consequently, an appropriate sense of three-dimensionality can be provided and necessary and sufficient brightness can be ensured even on the perimeter of a visual field.

(B1) $0.35 < NAr/NA_R < 0.85$

In the stereoscopic-vision endoscope of the fourth embodiment, it is more preferable to use a refractive index distribution type lens as the relay lens.

When a refractive index distribution type lens is used as the relay lens, the $NA_R$ and NAr values are expressed using angles β and γ.

$NA_R = \sin \beta$ $NAr = \sin \gamma$

Owing to the aforesaid configuration, the stereoscopic-vision endoscope of the fourth embodiment has become a thin and bright rigid endoscope. The employment of a pupil dividing means that satisfies the condition (B1) enables diagnostic observation through an image providing a sufficient sense of three-dimensionality that is a bright and high-quality image.

In the fourth embodiment, the lower limit of the condition (B1) is defined in order to enable observation through an image providing a sufficient sense of three-dimensionality. When the lower limit of 0.35 is exceeded, a sufficient sense of three-dimensionality may be unavailable. The upper limit is defined so that even when a pupil dividing means is displaced with respect to the optical axis of a optical system located in front of the pupil dividing means during machining or the like, light deficiency or variation derived from vignetting occurring in the perimeter of each image having parallax can be prevented. When the upper limit of the condition (B1) or 0.85 is exceeded, the light deficiency or variation may occur.

For the stereoscopic-vision endoscope of the fourth embodiment, it is conceivable to use a refractive index distribution type lens as a relay lens. When a refractive index distribution type lens is used as a relay lens, a superb stereoscopic-vision endoscope can be realized.

Next, the contents of the fourth embodiment will be described in detail by taking for instance a stereoscopic-vision endoscope using a refractive index distribution type lens as a relay lens.

In the fourth embodiment, when a relay lens realized with a refractive index distribution type lens is used instead of a relay lens composed of a plurality of homogeneous lenses, a large numerical aperture (NA) can be provided.

For transmitting an image using a relay lens composed of a plurality of homogeneous lenses, a spacing tube is needed to retain a space between each pair of lenses. Depending on the inner diameter of a spacing tube, the numerical aperture NA of a transmittable light beam is restricted. By contrast, a refractive index distribution type lens dose not require the spacing tube. Compared with the relay lens composed of homogeneous lenses having the same outer diameter, the relay lens realized with the refractive index distribution type lens permits a large numerical aperture. As far as the relay lens composed of a plurality of homogeneous lenses is concerned, many small lenses and spacing tubes must be set in array in an insertional part in the course of assembling a rigid endoscope. For the refractive index distribution type lens, one long lens alone should be inserted into an insertional part. Thus, the employment of the refractive index distribution type lens permits higher assembling efficiency than the employment of a plurality of homogenous lenses.

Next, a light transmission characteristic of a refractive index distribution type lens will be described.

Figure 16:
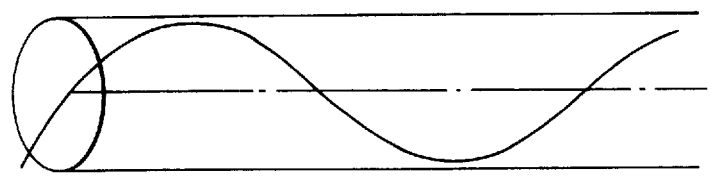
Figure 17:
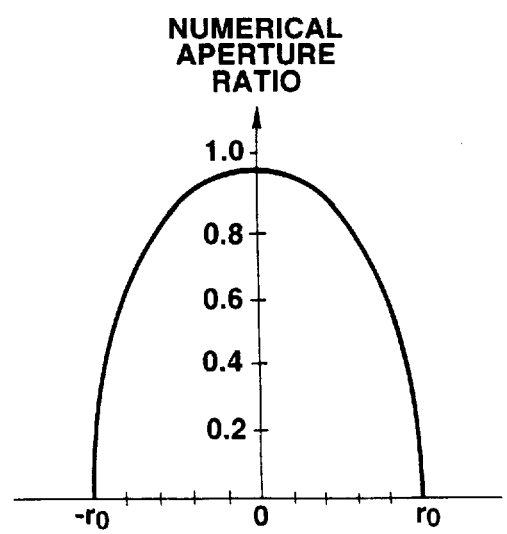

In general, a refractive index distribution type lens used for light transmission has a refractive index diminishing from the center toward the perimeter. Due to the effect of the refractive index distribution, light propagates, as shown in FIG. 16, while drawing a sine wave-like light path. When rays propagating through a refractive index distribution type lens draw a sine wave, the relationship of the ratio of a numerical aperture with the image height I in the refractive index distribution type lens are as listed in Table 13. FIG. 17 is a graph plotting the data listed in Table 13.

TABLE 13

| Image height I in the refractive index distribution type lens | Inter-numerical aperture ratio |
| --- | --- |
| 0 | 1 |
| 0.2r0 | 0.98 |
| 0.4r0 | 0.92 |
| 0.6r0 | 0.8 |
| 0.7r0 | 0.71 |
| 0.75r0 | 0.66 |
| 0.8r0 | 0.6 |
| 0.85r0 | 0.53 |
| 0.9r0 | 0.44 |
| r0 | 0 |

In Table 13 and FIG. 17, r0 denotes a radius of a refractive index distribution type lens.

As apparent from FIG. 17, when a refractive index distribution type lens is used as a relay lens, the ratio of a numerical aperture becomes maximum at the center of an image, decreases toward the perimeter thereof, and equals to zero on the circumference thereof.

Figure 18:
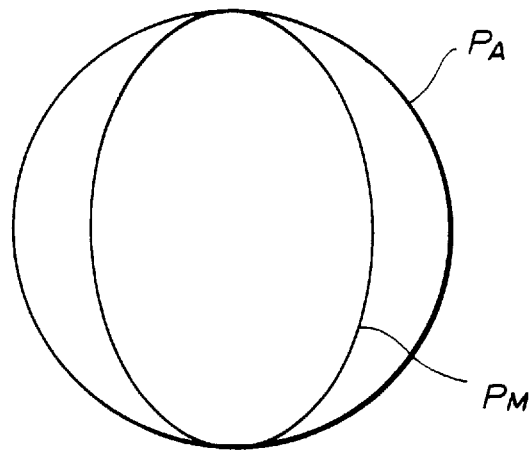
Figure 19:
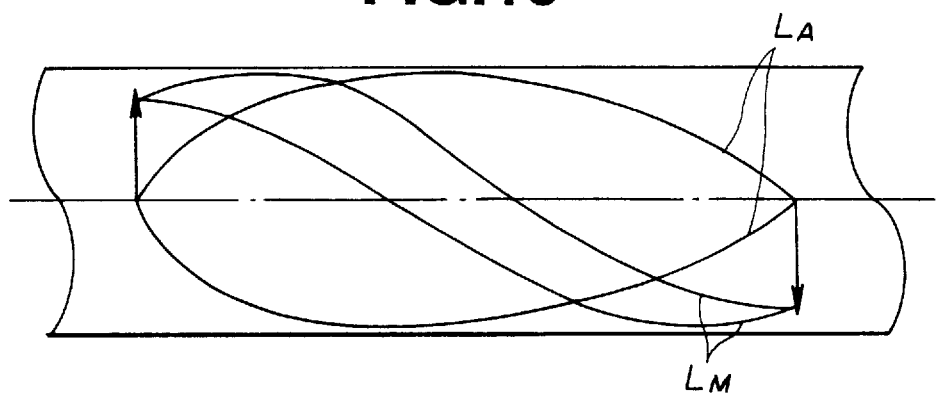

FIGS. 18 and 19 show numerical apertures relative to a maximum image height of 0.8r0. FIG. 18 shows a section of a light beam located in the vicinity of the positions of entrance pupils formed by a refractive index distribution type lens. FIG. 19 shows the routes of rays emanating from a point on the optical axis of a refractive index distribution type lens and of rays emanating from a point of a maximum image height. In FIG. 18, $P_A$ depicts a shape formed with rays emanating from the center of an image, and $P_M$ depicts a shape formed with rays emanating from the point of the maximum image height of the image. In FIG. 19, $L_A$ depicts the rays emanating from the point on the optical axis, and $L_M$ depicts the rays emanating from the point of the maximum image height. These drawings demonstrate that the ratio of a numerical aperture relative to the higher maximum image height is lower.

Figure 20:
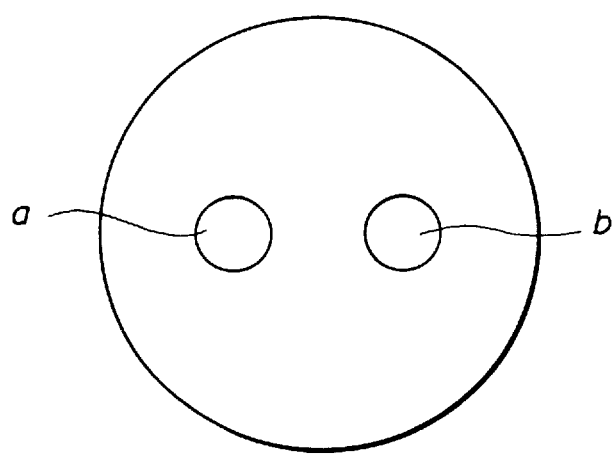
Figure 21:
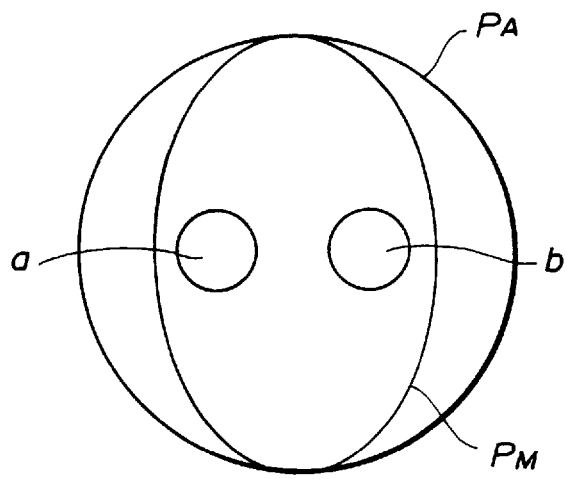
Figure 22:
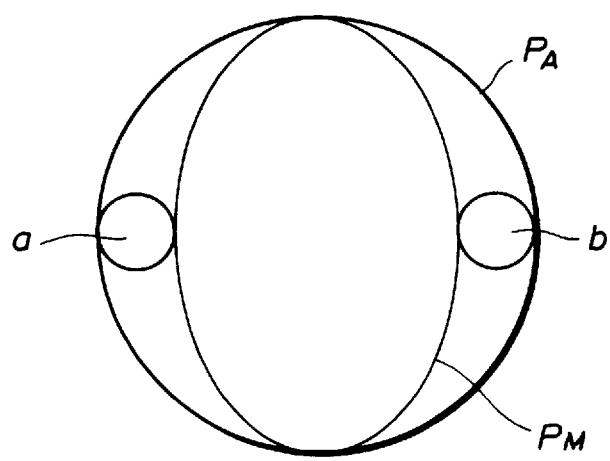

In the fourth embodiment, a pupil dividing means, for example, a pupil dividing stop shown in FIG. 20 is situated at a position conjugate to the positions of entrance pupils formed by a refractive index distribution type lens (relay lens). A light beam emanating from an object image is divided into two or more images having parallax. The pupil dividing stop has apertures a and b at substantially symmetric positions with respect to the optical axis of an optical system lying ahead of the pupil dividing stop. When the shapes of rays in the vicinity of the positions of entrance pupils shown in FIG. 18 are overlaid on the pupil dividing stop shown in FIG. 20, as shown in FIGS. 21 and 22, vignetting occurs in the perimeter of an image or an amount of light differs from image height to image height, though it depends on the spacing between the apertures a and b of the pupil dividing stop. FIG. 22 shows an example of a pupil dividing stop in which the spacing between the apertures a and b is too large. Rays traveling at a maximum image height fail to pass through the apertures a and b, while rays traveling near a maximum image height fail to form an image. This results in vignetting in the center of a visual field. FIG. 21 shows an example of a pupil diving stop in which the spacing between the apertures a and b is small. Since rays traveling at the maximum image height can pass through the apertures a and b, vignetting does not occur in the perimeter of a visual field. However, when a pupil dividing stop having the apertures shown in FIG. 22 is used, a sense of three-dimensionality is weak.

Figure 23:
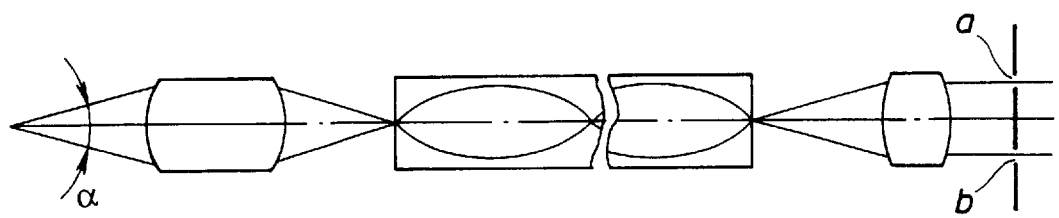
Figure 24:
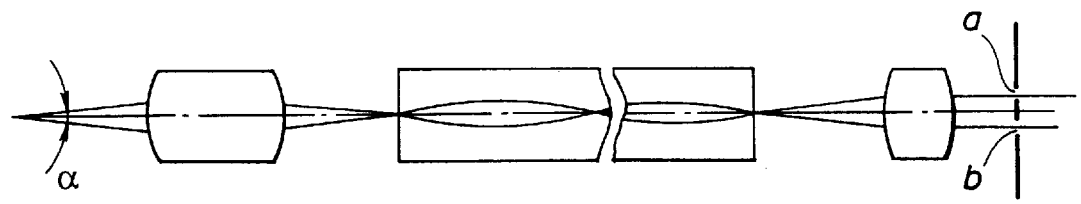

The relationship between an angle of introversion α that dominates a sense of three-dimensionality, and a spacing between the apertures a and b of a pupil dividing stop is as shown in FIGS. 23 and 24. FIG. 23 shows a route along which a light beam travels when the spacing between the apertures a and b is too large. FIG. 24 shows a route along which a light beam travels when the spacing between the apertures a and b is small. As apparent from FIGS. 23 and 24, the angle of introversion α that dominates a sense of three-dimensionality gets larger with an increase in spacing between the apertures a and b. The larger the angle of introversion α is, the more intense the sense of three-dimensionality becomes. Consequently, depth information can be more readily acquired.

As mentioned above, when the spacing between the apertures a and b of a pupil dividing stop is too large, vignetting occurs in the perimeter of a visual field. When the spacing between the apertures a and b thereof is too small, the sense of three-dimensionality becomes weak. It is therefore preferred that the spacing between the apertures a and b of a pupil dividing stop should be determined to such an extent that vignetting will not occur in the perimeter of a visual field and as intense a sense of three-dimensionality as possible can be provided. When the spacing between the apertures a and b of a pupil dividing stop are determined to such an extent that the centers of the apertures a and b will come within rays traveling at a maximum image height at the position of the pupil dividing means, vignetting that is so severe as to pose a problem in practice will not occur in the perimeter of a visual field.

In the stereoscopic-vision endoscope of the fourth embodiment, it is preferred that the spacing between the apertures a and b of a pupil dividing means to be situated at a position conjugate to the positions of entrance pupils formed by a relay lens is determined so that the centers of the apertures will lie within rays traveling at a maximum image height at the position of the pupil dividing means.

The spacing between the apertures should preferably be within the above range and satisfy requirements including the one that a sufficient sense of three-dimensionality must be provided.

The above description has proceeded on the assumption that a refractive index distribution type lens is used as a relay lens. The same applies to a relay lens composed of homogeneous lenses.

The pupil dividing stop has the apertures a and b at substantially symmetric positions with respect to the optical axis of an optical system lying ahead of the pupil dividing stop. As far as this kind of pupil dividing stop is concerned, the positions of apertures may be deviated from the optical axis of the optical system lying ahead of the pupil dividing stop. In this case, vignetting may occur in the perimeter of an image.

The condition (1) has been devised for the foregoing reasons. When the quotient of $NAr/NA_R$ exceeds the lower limit of the condition (1), no sense of three-dimensionality is provided. When the quotient of $NAr/NA_R$ exceeds the upper limit thereof, if the positions of the apertures a and b are deviated from the optical axis of an optical system lying ahead of a pupil dividing stop, vignetting may occur in the perimeter of an image having parallax or an amount of light may vary.

The above description has proceeded on the assumption that a refractive index distribution type lens is used as a system of relay lenses for a stereoscopic-vision rigid endoscope of the fourth embodiment. In an endoscope having an optical system in which a relay lens composed of homogenous lenses is used to transmit an image; such as, the one of the seventh embodiment that will be described later, when the condition (1) is satisfied, the relationship of the ratio of a numerical aperture with the image height I of an image relayed by the relay lens will be as shown in FIG. 17.

In the fourth embodiment, when a refractive index distribution type lens is used as a relay lens to transmit rays emanating from small image heights or when homogeneous lenses permitting the ratio of a numerical aperture that becomes higher relative to larger image heights are used as a relay lens, if the condition (1) is satisfied, the endoscope would be effective for observation through a bright image with an appropriate sense of three-dimensionality.

When a refractive index distribution type lens is used as a relay lens to transmit rays emanating from large image heights, or when homogeneous lenses, in each of which the ratio of a numerical aperture becomes lower relative to larger image heights, are used as a relay lens, it is preferred to satisfy the condition below for observation through a bright image with an appropriate sense of three-dimensionality.

$0.35 < NAr/NA_R < 0.75$

Next, the particular configuration of the fourth embodiment will be described on the basis of the aforesaid description of the concept.

Figure 25:
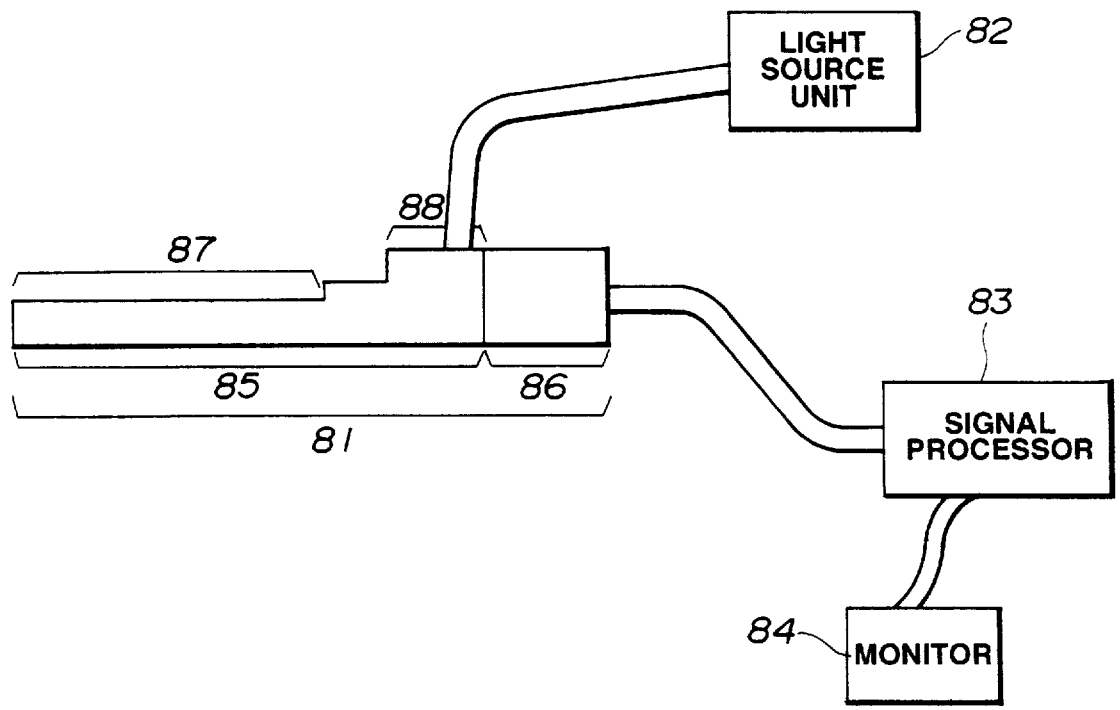

A stereoscopic-vision rigid endoscope system shown in FIG. 25 comprises a stereoscopic-vision rigid endoscope 81, a light source unit 82, a signal processor 83 for processing electric signals provided by imaging devices and converting them into video signals, and a monitor 84 for displaying the video signals. The monitor 84 displays alternately right and left images provided by a pupil dividing stop. A viewer wears glasses having the capability of a shutter so as to have a stereoscopic vision.

The stereoscopic-vision rigid endoscope 81 consists of a direct-vision scope 85, and a camera head 86 detachably coupled to the scope 85. A skew-vision scope may be detachably coupled to the camera head 86 on behalf of the direct-vision scope. Since the scope 85 and camera head 84 are detachable, a plurality of scopes having different specifications can be selectively used in combination with one camera head. When a mechanism allowing the scope 85 and camera head 86 to make a relative rotation is installed in the vicinity of the junction between the scope 85 and camera head 86, even if the scope 85 is turned, since the scope accommodates one optical system, an image will not turn.

Figure 26:
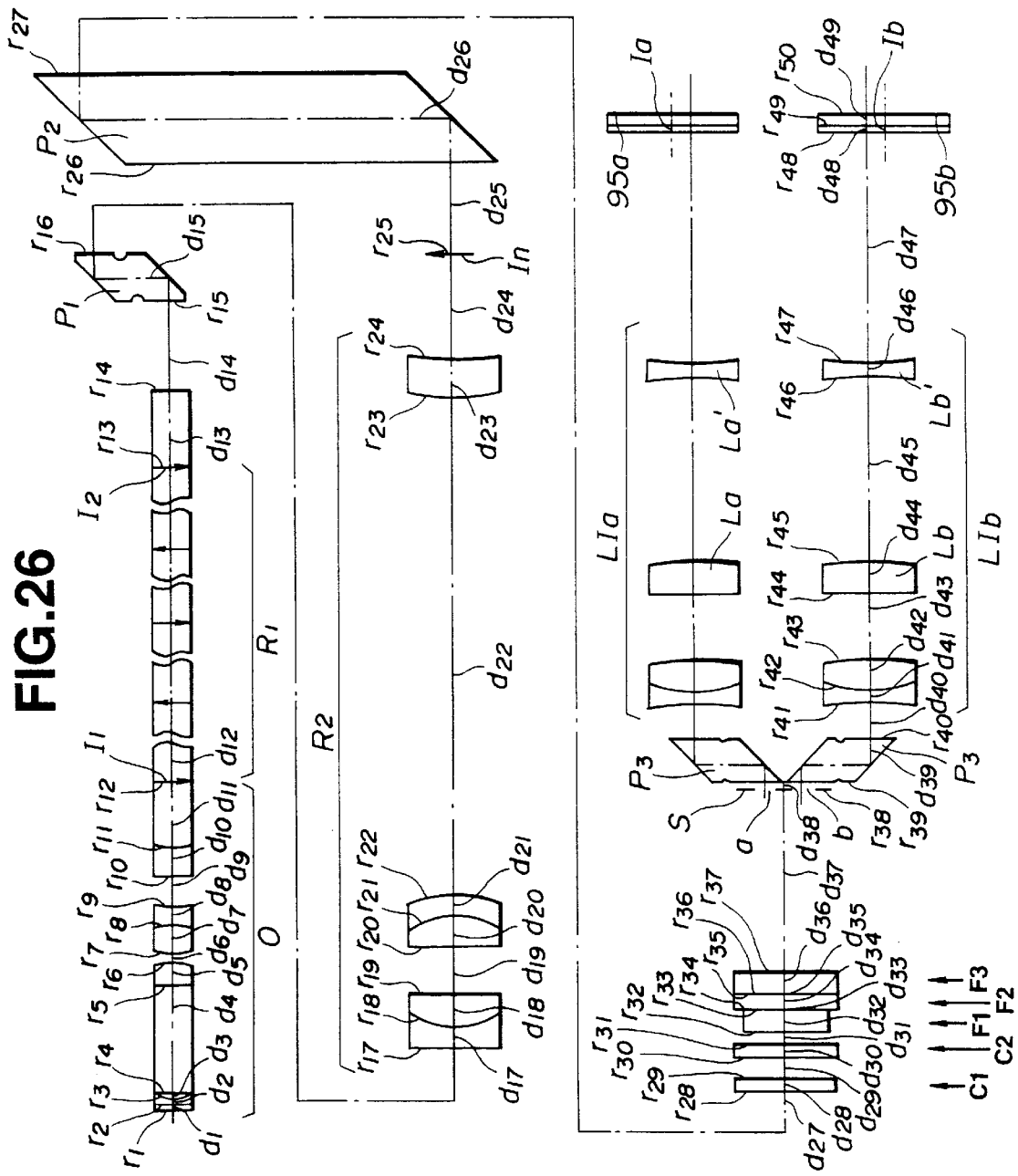

An optical system in the stereoscopic-vision rigid endoscope 81 is, as shown in FIG. 26, composed of an objective optical system O, a relay optical system R composed of relay lenses R1 and R2, a pupil dividing stop S, an image formation optical system LI, and imaging devices 95a and 95b which are arranged in an insertional part in that order starting from the outermost object space.

In the above optical system, the objective optical system lying in the distal portion of an insertional part 87 shown in FIG. 26 forms an object image at a position of image formation. The outer diameter of an objective lens is about 2.1 mm. A juncture lens (r10 to r12) is joined with one end in the object space of a refractive index distribution type lens (r12 to r13) constituting the relay lens R1. In the juncture lens, the lens (r10 to r11) has a lower refractive index than a refractive index lens (r11 to r12). When the juncture lens (r10 to r12) is joined with one end in the object space of the relay lens R1, the heights of rays can be made lower. Moreover, it can be prevented that dust adheres to the surface of the refractive index distribution type lens. The dust or flaws will therefore not impair an image.

In the optical system shown in FIG. 26, the objective lens O forms an object image, and the refractive index distribution type lens (r12 to r13) constituting the relay lens R1 forms an image I2 on the back end of the refractive index distribution type lens. For preventing the flaws on or dust adhering to the surface of the refractive index distribution type lens from being projected on the back end r13 of the refractive index distribution type lens (r12 to r13), a lens (r13 to r14) is attached to the back end r12. Behind the lens, a prism P1 shaped like a parallelogram is placed in order to displace the optical axis of the refractive index distribution type lens.

In this embodiment, the optical axis of the refractive index distribution type lens is angled using the prism P1. In the scope 5, a frame accommodating a surgical therapeutic instrument is incorporated substantially in contact with a frame accommodating lenses. For minimizing invasion to a patient, a surgical therapeutic instrument should come out through a narrow space in the vicinity of the insertional part 7 of the scope 5. In a small-diameter rigid scope of this embodiment, a therapeutic instrument is placed in parallel with an optical system and designed to come out from the distal end of the scope in parallel with the optical system.

When the relay lens R2 placed behind the relay lens (refractive index distribution type lens) R1 is used to transmit an image to imaging devices 15a and 15b located behind the relay lens R2, the image must be relayed at a nonzero power. The relay lens R2 has therefore a larger diameter. The prism P1 shaped like a parallelogram is placed at the position shown in FIG. 26 in order to angle the optical axis of the refractive index distribution type lens. Thus, the frame accommodating a therapeutic instrument and the frame accommodating lenses are prevented from interrupting with each other.

After the optical axis is angled, the relay lens R2 placed behind the prism P1 relays the image I2, which is formed in the vicinity of the other end in the image space of the refractive index distribution type lens, at a power of 2.15 and forms a final image In. The relay lens R2 also plays a role of correcting axial chromatic aberration caused by the refractive index distribution type lens (r12 to r13). The relay lens R2 is therefore designed to successfully correct a chromatic difference of magnification and to produce aberration that cancels out the axial chromatic aberration caused by the refractive index distribution type lens R1. In addition, the relay lens R2 is situated so that abaxial rays can pass through the apertures of the pupil dividing stop; that is, the exit pupils of a stop will be formed by the image formation optical systems LI situated behind the relay lens R2. A visual field mask is placed at a position at which the final image In is formed.

A light beam emanating from the final image In formed by the relay optical system R passes through the prism P2 for displacing the optical axis, travels through cover glasses C1 and C2 and optical devices F1 to F3 such as optical filters, and then is divided into a plurality of portions (in this embodiment, two portions) by a S that has two apertures, serves as a pupil dividing means, and lies in the vicinity of the positions of exit pupils. Resulting light beams are widely spaced by a prism P3 shaped like a parallelogram. Two images Ia and Ib having parallax are then formed on imaging devices 95a and 95b by means of the image formation optical systems LIa and LIb. The optical devices F1 to F3 are optical filters that may be infrared cutoff filters, YAG laser cutoff filters, or optical low-pass filters.

The portion of the optical system of this embodiment ending with the color glass C1 behind the prism P2 constitutes the scope 5.

The stereoscopic-vision rigid endoscope 81 of the fourth embodiment can provide necessary and sufficient brightness even in the perimeter of a visual field and offer an appropriate sense of three-dimensionality despite the insertional part 87 having a small outer diameter. For explaining this advantage of the fourth embodiment, a section of a light beam in relation to the positions of exit pupils is shown in FIG. 27.

Figure 27:
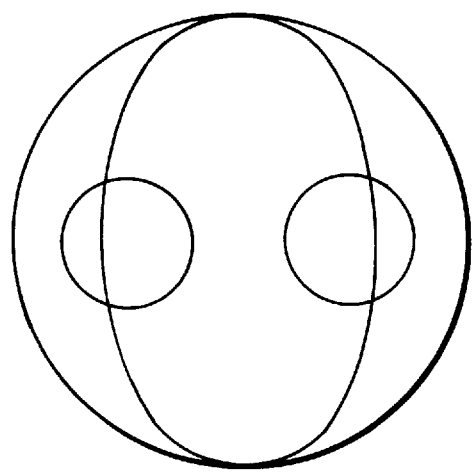

In FIG. 27, an outer circle depicts the shape formed with rays determining the numerical aperture on the optical axis. An ellipse depicts the shape formed with rays determining the numerical aperture at a maximum image height. The stop S serving as a pupil dividing means has apertures a and b having a radius of 0.9 mm and encircling symmetric points each distanced by 1.4 mm from the center of the circle or the circumference of the stop. The numerical aperture at each of the apertures a and b of the stop S is three-tenths of the numerical aperture at the center of a refractive index distribution type lens. Rays emanating from a point of a maximum image height occupy two-thirds of a light beam passing through the apertures a and b. At this time, an angle of introversion α is about 1.3° relative to a distance from an object of 7 mm. Although the diameters of lenses incorporated in the insertional part 7 are as small as 2.1 mm, even when the apertures a and b of the pupil dividing stop S are displaced with respect to the optical axis of an optical system lying ahead of the stop, sufficient brightness can be ensured even for the perimeter of a visual field and a sufficient sense of three-dimensionality can be provided.

Data concerning the optical system for the fourth embodiment of the present invention are listed below.

TABLE 14

Distance from an object = −7, Height of a final image formed by the relay optical system = 1.72, Height of a final image formed by the objective optical system = 0.8
Angle of view = 50.1°, Angle of introversion relative to a distance from an object of −7 = 1.3°

| | | | |
|---|---|---|---|
| r1 = ∞ | d1 = 0.3000 | n1 = 1.51633 | ν1 = 64.15 |
| r2 = ∞ | d2 = 0.2500 | n2 = 1.69680 | ν2 = 55.53 |
| r3 = 1.2400 | d3 = 0.2700 | | |
| r4 = ∞ | d4 = 6.0000 | n3 = 1.80610 | ν3 = 40.95 |
| r5 = ∞ | d5 = 1.2000 | n4 = 1.83400 | ν4 = 37.17 |
| r6 = −3.2790 | d6 = 0.5000 | | |
| r7 = 2.9180 | d7 = 1.6000 | n5 = 1.58913 | ν5 = 61.18 |
| r8 = −2.2780 | d8 = 1.0000 | n6 = 1.78472 | ν6 = 25.68 |
| r9 = 4.1030 | d9 = 1.6400 | | |
| r10 = ∞ | d10 = 1.5000 | n7 = 1.48749 | ν7 = 70.21 |
| r11 = 2.4160 | d11 = 3.5800 | n8 = 1.88300 | ν8 = 40.78 |
| r12 = ∞ | d12 = 201.0000 | n9 (Refractive index distribution type lens) | |
| r13 = ∞ | d13 = 4.0000 | n10 = 1.51633 | ν10 = 64.15 |
| r14 = −6.2000 | d14 = 5.0000 | | |
| r15 = ∞ | d15 = 6.5000 | n11 = 1.80610 | ν11 = 40.95 |
| r16 = ∞ | d16 = 2.7200 | | |
| r17 = ∞ | d17 = 1.5000 | n12 = 1.69895 | ν12 = 30.12 |
| r18 = 5.2880 | d18 = 2.5000 | n13 = 1.69680 | ν13 = 55.53 |
| r19 = ∞ | d19 = 3.7200 | | |
| r20 = 58.5770 | d20 = 2.5000 | n14 = 1.69680 | ν14 = 55.53 |
| r21 = −5.1250 | d21 = 1.5000 | n15 = 1.80518 | ν15 = 25.43 |
| r22 = −11.4220 | d22 = 42.7800 | | |
| r23 = 12.5580 | d23 = 3.0000 | n16 = 1.59270 | ν16 = 35.29 |
| r24 = 33.5740 | d24 = 8.0000 | | |
| r25 = ∞ | d25 = 7.0000 | | |
| r26 = ∞ | d26 = 35.0000 | n17 = 1.80610 | ν17 = 40.95 |
| r27 = ∞ | d27 = 9.3000 | | |
| r28 = ∞ | d28 = 1.0000 | n18 = 1.51633 | ν18 = 64.15 |
| r29 = ∞ | d29 = 1.9500 | | |
| r30 = ∞ | d30 = 1.0000 | n19 = 1.51633 | ν19 = 64.15 |
| r31 = ∞ | d31 = 3.0000 | | |
| r32 = ∞ | d32 = 1.6700 | n20 = 1.54814 | ν20 = 45.78 |
| r33 = ∞ | d33 = 0.1000 | | |

TABLE 14-continued

Distance from an object = −7, Height of a final image formed by the relay optical system = 1.72, Height of a final image formed by the objective optical system = 0.8
Angle of view = 50.1°, Angle of introversion relative to a distance from an object of −7 = 1.3°

| | | | |
|---|---|---|---|
| r34 = ∞ | d34 = 1.0000 | n21 = 1.52287 | v21 = 59.89 |
| r35 = ∞ | d35 = 0.1000 | | |
| r36 = ∞ | d36 = 1.6000 | n22 = 1.51400 | v22 = 74.00 |
| r37 = ∞ | d37 = 3.0000 | | |
| r38 = ∞ | d38 = 0.5000 | | |
| (Brightness stop) | | | |
| r39 = ∞ | d39 = 8.5400 | n23 = 1.80610 | v23 = 40.95 |
| r40 = ∞ | d40 = 2.7200 | | |
| r41 = −25.1610 | d41 = 1.0000 | n24 = 1.69895 | v24 = 30.12 |
| r42 = 9.4380 | d42 = 2.5000 | n25 = 1.69680 | v25 = 55.53 |
| r43 = −17.7560 | d43 = 5.0000 | | |
| r44 = 121.7100 | d44 = 2.5000 | n26 = 1.76182 | v26 = 26.55 |
| r45 = −25.9750 | d45 = 17.9200 | | |
| r46 = −16.7230 | d40 = 1.0000 | n27 = 1.69680 | v27 = 55.53 |
| r47 = 35.3840 | d47 = 24.2500 | | |
| r48 = ∞ | d48 = 0.4000 | n28 = 1.51633 | v28 = 64.15 |
| r49 = ∞ | d49 = 0.7500 | | |
| r50 = ∞ | | | |

$NAr/NA_R = 0.61$

Reference numerals r1, r2, etc. denote radii of curvature of lenses. d1, d2, etc. denote thicknesses of the lenses and spacings between lenses. n1, n2, etc. denote refractive indices of the lenses. v1, v2, etc. denote Abbe numbers of the lenses.

The approximation of the distribution of refractive indices of a refractive index distribution type lens can be provided according to the following expression:

$$N(r) = n0\{1 - (\tfrac{1}{2})Ar^2\}$$

where N(r) denotes a refractive index at a position deviated by a distance r from the optical axis. n0 denotes a refractive index on the optical axis and equals to 1.610 (λ=555 nm). A denotes a refractive index distribution coefficient and is expressed as follows:

$$\sqrt{A} = 0.6236$$

Figure 28:
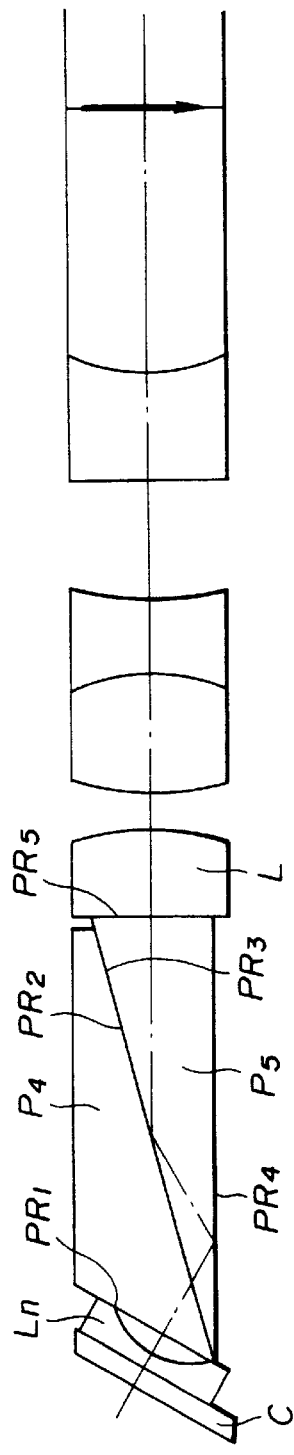

Next, a stereoscopic-vision rigid endoscope for skew vision that is a variant of the fourth embodiment will be described. An elongated lens (r4 to r5) lying in the distal portion of the objective lens O included in the optical system for the direct-vision rigid endoscope shown in FIG. 26 is replaced with 30° skew-vision prisms P4 and P5 shown in FIG. 28. Thus, a stereoscopic-vision rigid endoscope for skew vision is realized.

In the rigid endoscope of a variant of the fourth embodiment having the distal portion constructed as mentioned above, light enters an incident surface PR1 of the prism P4, is transmitted by a transmission surface PR2 and a surface PR3 of the prism P5 in that order, totally reflected from a surface PR4 and a surface PR3 in that order, and then emitted from a surface PR5. Rays entering the surface PR5 of the prism P5 after passing through the transmission surface PR2 of the prism P4 and an adhesive are transmitted by the surfaces PR2 and PR3 because the angles of incidence on the surfaces PR2 and PR3 exceeds the angles of total reflection.

The surface PR4 of the prism P5 is coated with a membrane having a lower refractive index than the prism P5. Part of rays entering the surface PR4 through the surface PR3 of the prism 5, which has an angle of incidence that is larger than an angle of total reflection dependent on a difference in refractive index between the glass and membrane and which contributes to image formation, is reflected totally from the boundary between the prism surface PR4 and membrane. Rays, which do not contribute to image formation and have an angle of incidence that is smaller than the angle of total reflection, are absorbed by an absorbent layer coated on the membrane.

The rays totally reflected from the surface PR4 enter the surface PR3 and are totally reflected because the angle of incidence becomes larger than the angle of total reflection dependent on a difference in refractive index between the glass of the prism P5 and adhesive.

A distal cover glass C and concave lens Ln of the objective optical system O are arranged askew with respect to the longitudinal direction of a scope 85 so that the optical axes thereof will align with the optical axis of the 30° skew-vision prism P4. The cover glass and concave lens are attached to each other. The cover glass C has sides thereof cut askew with respect to the surface thereof to such an extent that it can be stewed in the insertional part 7. The surface of the cover glass C is shaped like an ellipse. An optical system lying in the image space beyond the lens L has the same components as the optical system lying in the image space beyond the lens L in the stereoscopic-vision rigid endoscope for direct vision shown in FIG. 26 of the fourth embodiment.

In the stereoscopic-vision rigid endoscope 81 of the fourth embodiment, the scope 85 and camera head 86 are constructed separately. Focusing can be carried out independently for the scope 85 and camera head 86 in the course of assembly. Focusing of the scope 85 is carried out by moving back and forth a refractive index distribution type lens using a mechanism for moving the refractive index distribution type lens along the optical axis. Focusing of the camera head 86 is carried out by moving the lenses La, Lb, L'a, and L'b included in the image formation optical systems LIa and LIb using a mechanism for moving the lenses along the optical axes thereof.

For focusing of the camera head 86, it is preferred to include a mechanism for decentering the imaging devices 95a and 95b by moving them on planes perpendicular to the optical axes thereof or for adjusting the directions of rotations on the planes perpendicular to the optical axes of the imaging devices 95a and 95b made by the imaging devices 95a and 95b.

Due to the employment of the mechanism, when the scope 85 and camera head 86 are coupled mutually, excellent stereoscopic visioning is enabled.

Figure 29:
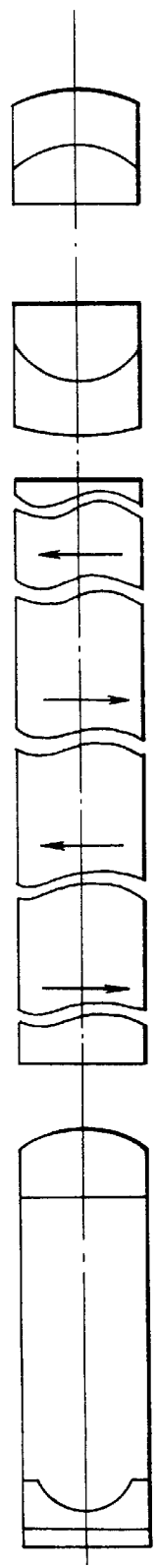
FIG. 29 shows part of an optical system for a stereoscopic-vision rigid endoscope in accordance with the fifth embodiment of the present invention.

FIG. 29 shows the components of an optical system lying in the vicinity of a refractive index distribution type lens (relay lens) in accordance with the fifth embodiment of the present invention. This embodiment differs from the fourth embodiment in a point that an image is formed at both ends of the refractive index distribution type lens.

The foregoing structure prevents dust adhering to both the ends of the refractive index distribution type lens or flaws on the ends thereof from being projected. Consequently, unlike the fourth embodiment, homogeneous lenses need not be joined with both the ends of the refractive index distribution type lens.

When the optical system lying behind the relay lenses in the fourth embodiment shown in FIG. 46 is connected to the back of the optical system shown in FIG. 29, a stereoscopic-vision rigid endoscope permitting an appropriate sense of three-dimensionality and brightness can be realized.

It is conceivable that by varying the length of a refractive index distribution type lens, an image formed at one end of the refractive index distribution type lens in the object space may be transmitted to form an image on the other end thereof in the image space, or an image may be transmitted so that exit pupils can be formed.

Figure 30:
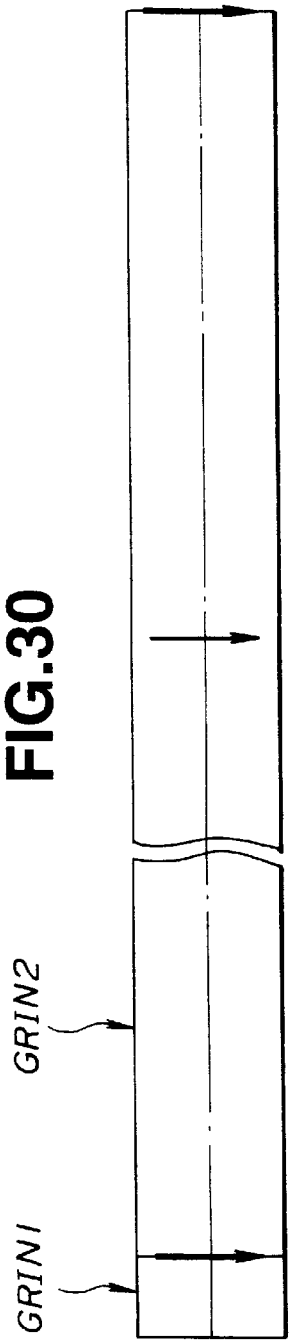
FIG. 30 shows part of an optical system for a stereoscopic-vision rigid endoscope in accordance with the sixth embodiment of the present invention.

FIG. 30 shows part (objective lens and a system of relay lenses) of an optical system in accordance with the sixth embodiment of the present invention. In this embodiment, a refractive index distribution type lens is used as each of an objective lens and a system of relay lenses. In FIG. 30, a refractive index distribution type lens GRIN1 serves as an objective lens and a refractive index distribution type lens GRIN2 serves as a system of relay lenses. This structure makes it possible to realize a stereoscopic-vision rigid endoscope of simple configuration.

In this embodiment, the numerical aperture NA permitted by the refractive index distribution type lens GRIN1 serving as an objective lens at the center thereof is 0.5, and the numerical aperture permitted by the refractive index distribution type lens GRIN2 serving as a system of relay lenses is 0.1.

Even in the sixth embodiment, a stereoscopic-vision rigid endoscope offering an appropriate sense of three-dimensionality and proper brightness and accomplishing the object of the present invention can be realized by connecting the optical system lying behind the system of relay lenses in the fourth embodiment to the back of the optical system shown in FIG. 30.

Figure 31:
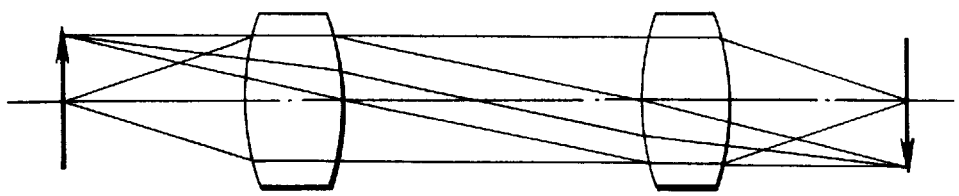
FIG. 31 shows part of an optical system for a stereoscopic-vision rigid endoscope in accordance with the seventh embodiment of the present invention.

FIG. 31 shows part (system of relay lenses) of an optical system for the seventh embodiment of the present invention. The seventh embodiment employs a system of homogeneous lenses as a system of relay lenses.

In the seventh embodiment, unlike the fourth to sixth embodiments, a refractive index distribution type lens is not used as a system of relay lenses. Axial chromatic aberration can be corrected readily using the system of relay lenses. That is to say, a field lens is used as a final relay lens so that abaxial rays will pass through apertures of a stop.

In this embodiment, the relationship of a numerical aperture ratio with a height I of an image formed by a system of relay lenses is graphically illustrated in FIG. 17. When the objective lens for the first embodiment is placed ahead of the system of relay lenses and a camera head is connected to the back of the system of relay lenses, a stereoscopic-vision rigid endoscope offering an appropriate sense of three-dimensionality and appropriate brightness can be realized.

Next, mention will be made of another arrangements of an optical system for a camera head which are adaptable to a stereoscopic-vision rigid endoscope in accordance with any of the fourth to seventh embodiments.

Figure 32:
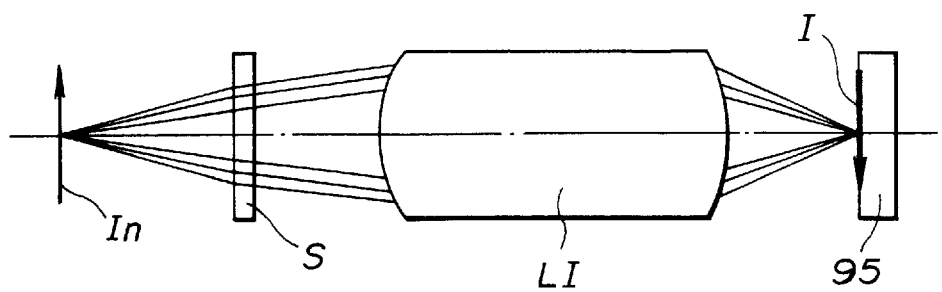
FIG. 32 shows another example of an optical system for a camera head in a stereoscopic-vision rigid endoscope adaptable to the fourth to seventh embodiments.
Figure 33:
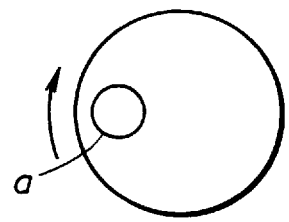
FIG. 33 shows the components of a pupil dividing stop situated at a position conjugate to the positions of entrance pupils formed by a system of relay lenses in the stereoscopic-vision rigid endoscope shown in FIG. 32.

FIGS. 32 to 35 schematically show another examples of an optical system for the camera head 6 corresponding to a portion of the optical system for the fourth embodiment shown in FIG. 26 from the final image In (r25) formed by the relay optical system R to the imaging devices 95a and 95b. Above all, in FIG. 32, a pupil dividing means S, one image formation optical system LI, and one imaging device 95 which are situated in the vicinity of the positions of exit pupils are arranged in that order behind the final image In of the system of relay lenses. Unlike the pupil dividing stop shown in FIG. 20, the pupil dividing means S has one aperture a in the disk thereof as shown in FIG. 33 and is turned with the center of the disk as a rotation center by means of a rotating mechanism that is not shown. The imaging device 95 has the capability of a device shutter and samples a video signal synchronously with the rotation of the disk.

Using the optical system for a camera head shown in FIG. 32, the position of the aperture a is changed with the rotation of the disk that is the pupil dividing means. An image formed with rays passing through the aperture is received by the same imaging device. A video signal representing the image is acquired fraction by fraction. Thus, stereoscopic visioning can be enabled in the same manner as that in the first embodiment.

Figure 34:
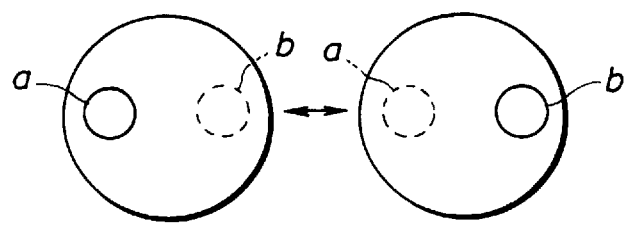
FIG. 34 shows a liquid-crystal shutter serving as a pupil dividing stop situated at a position conjugate to the positions of the entrance pupils formed by the system of relay lenses in the stereoscopic-vision rigid endoscope shown in FIG. 32.

In the optical system for a camera head shown in FIG. 32, a liquid-crystal shutter may be used as a pupil dividing means. The liquid-crystal shutter provides, as shown in FIG. 34, apertures a and b alternately. When the pupil dividing means shown in FIG. 34 is used, the imaging device need not have the capability of a device shutter.

In a pupil dividing means included in the optical system for a camera head, the lateral spacing between the positions of an aperture defined with the rotation of the disk or the lateral spacing between the positions of an area of a liquid-crystal shutter serving as an aperture satisfies the condition (1).

Figure 35:
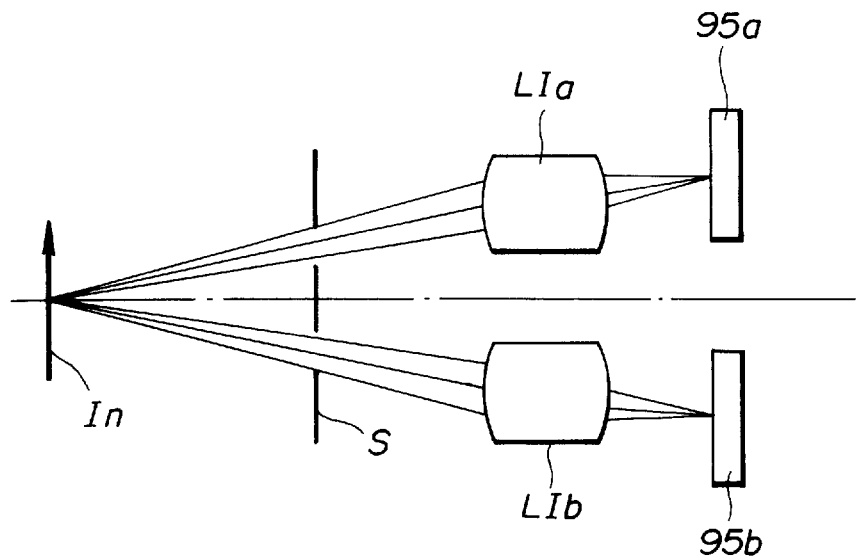
FIG. 35 shows yet another example of an optical system for a camera head in a stereoscopic-vision rigid endoscope adaptable to the fourth to seventh embodiments.
Figure 36:
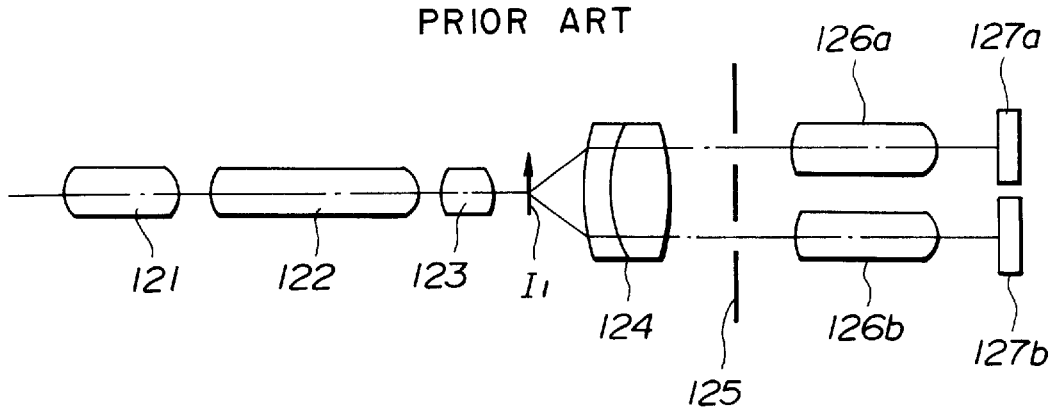
FIG. 36 shows the components of an optical system for a stereoscopic-vision rigid endoscope in accordance with a prior art.
Figure 37:
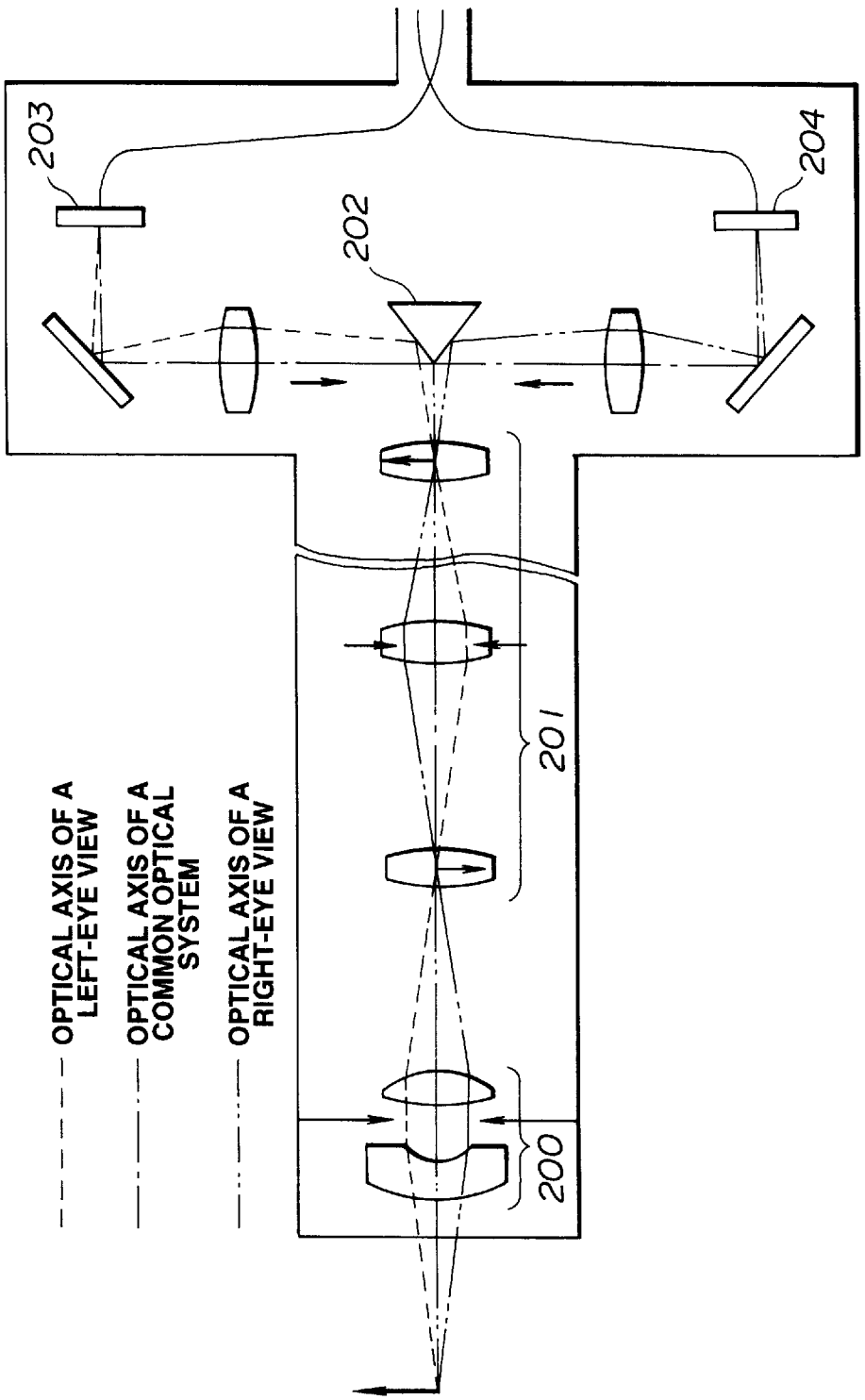
FIG. 37 shows the configuration of the stereoscopic-vision rigid endoscope in accordance with the prior art.
Figure 38:
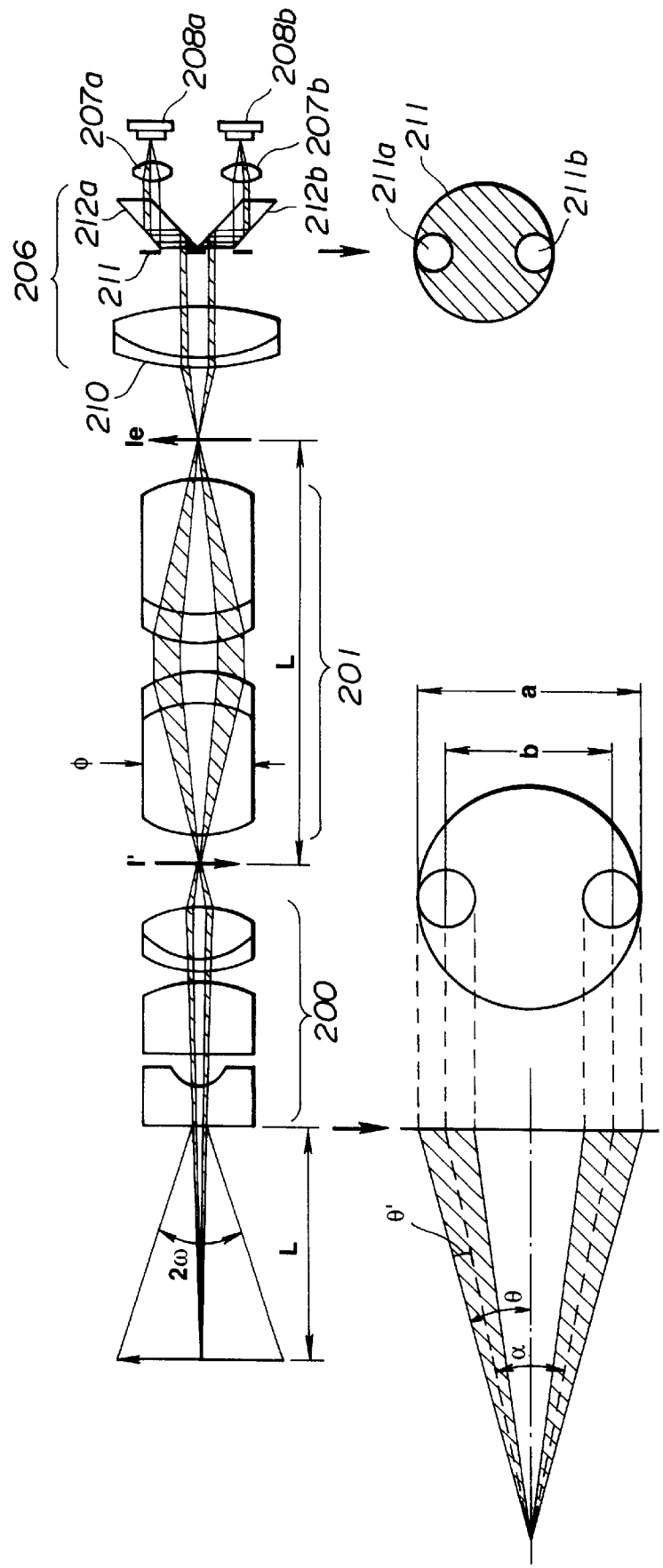
FIG. 38 shows the components of an imaging optical system for the stereoscopic-vision rigid endoscope in accordance with the prior art.
Figure 39:
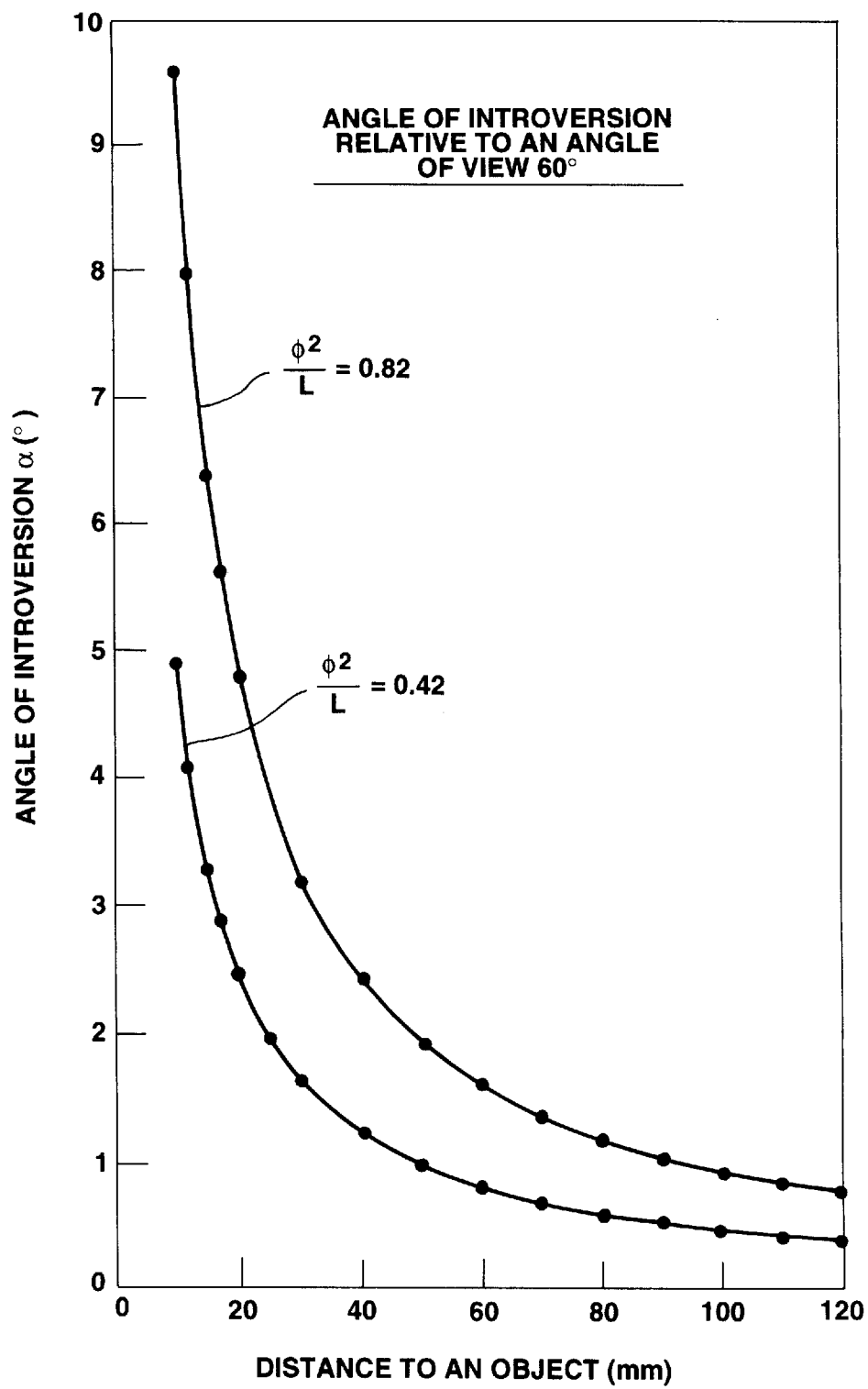
FIG. 39 is a graph showing the relationship of the distance from an object with the angle of introversion in accordance with the prior art.

FIG. 35 shows yet another example of an optical system for a camera head. This optical system includes two image formation optical systems LIa and LIb on behalf of a parallelogram-shaped prism to be placed behind a pupil dividing stop. A rotary disk or a liquid-crystal shutter may be used as a pupil dividing means.

When a camera head having the optical system shown in any of FIGS. 32 to 35 is connected to the scope in any of the fourth to seventh embodiments, a stereoscopic-vision rigid endoscope offering an appropriate sense of three-dimensionality and appropriate brightness can be realized.

For the stereoscopic-vision rigid endoscope of this embodiment, a scope and a camera head may be designed to be separable mutually or separable at any other position, or may be designed as a united body.

According to the present invention, it will be apparent that a wide range of different embodiments can be formed on the basis of the invention without departure from the spirit and scope of the invention. The present invention will be limited to the appended claims but not restricted to any specific embodiments.

What is claimed is:

1. A stereoscopic-vision endoscope, comprising:

a tubular elongated insertional part;

an objective optical system situated in the distal portion of said insertional part;

a relay optical system situated in said insertional part for transmitting an object image formed by said objective optical system;

a pupil dividing means for dividing a light beam emanating from an object image formed by said relay optical system into a plurality of portions;

image formation optical systems for receiving light beams from said pupil dividing means so as to form a plurality of object images having parallax; and imaging means for picking up object images formed by said image formation optical system;

said relay optical system including a system of relay lenses that satisfies the following condition (A1):

condition (A1): $\phi^2/L>0.573$ where $\phi$ denotes an outer diameter of said system of relay lenses and L denotes a relay length of said system of relay lenses.

2. The stereoscopic-vision endoscope according to claim 1, wherein said relay optical system includes a system of relay lenses satisfying the following condition (A5):

condition (A5): $f/L \leq 0.248$

3. The stereoscopic-vision endoscope according to claim 1, wherein an aspheric plane is adopted as a concave surface in the image space of a distal concave lens of said objective optical system.

4. The stereoscopic-vision endoscope according to claim 1, wherein said objective optical system includes a group of concave lenses in the object space thereof beyond a virtual stop and a group of convex lenses in the image space thereof beyond the virtual stop, said group of convex lenses include at least two meniscus lenses, and a meniscus lens of said group of convex lenses situated in the outermost object space of said objective optical system has a concave surface in the object space of the meniscus lens.

5. The stereoscopic-vision endoscope according to claim 1, wherein said objective optical system includes a skew-vision prism.

6. The stereoscopic-vision endoscope according to claim 5, wherein said skew-vision prism includes a first prism and a second prism in that order starting from the outermost object space of said objective optical system; said first prism has a first surface and a second surface, said second prism has a first surface, a second surface, and a third surface; said second surface of said second prism is substantially parallel to the optical axis of said relay optical system; said second surface of said first prism and said first surface of said second prism are attached to each other with an adhesive; light emanating from an object passes through said first surface, comes out of said second surface, and then enters said first surface of said second prism; said light is then totally reflected from said second surface of said second prism, totally reflected from said first surface of said second prism, and then emitted from said third surface; and an orientation of a visual field ranges from 25° to 40°.

7. The stereoscopic-vision endoscope according to claim 1, wherein said pupil dividing means includes two or more groups of lenses including a juncture lens.

8. The stereoscopic-vision endoscope according to any of claims 1, and 7, wherein said pupil dividing means includes a pupil dividing stop having a plurality of apertures.

9. The stereoscopic-vision endoscope according to claim 8, wherein the diameters of said plurality of apertures of said pupil dividing stop are variable.

10. The stereoscopic-vision endoscope according to claim 8, wherein the shapes of said plurality of apertures of said pupil dividing stop are larger along the circumference of said stop than along a radius thereof.

11. The stereoscopic-vision endoscope according to claim 8, wherein centers of gravity of said plurality of apertures of said pupil dividing stop are variable.

12. A stereoscopic-vision endoscope, comprising:

a tubular elongated insertional part;

an objective optical system situated in the distal portion of said insertional part;

a relay optical system situated in said insertional part for transmitting an object image formed by said objective optical system;

a pupil dividing means for dividing a light beam emanating from an object image formed by said relay optical system into a plurality of portions;

image formation optical systems for receiving light beams from said pupil dividing means so as to form a plurality of object images having parallax; and imaging means for picking up object images formed by said image formation optical system;

said relay optical system including a system of relay lenses that satisfies the following condition (A3):

condition (A3): $\phi/L > 0.078$ where $\phi$ denotes an outer diameter of said system of relay lenses and L denotes a relay length of said system of relay lenses.

13. A stereoscopic-vision endoscope, comprising:

a tubular elongated insertional part;

an objective optical system situated in the distal portion of said insertional part;

a relay optical system situated in said insertional part for transmitting an object image formed by said objective optical system;

an illumination light transmitting means situated in said insertional part;

a pupil dividing means for dividing a light beam emanating from an object image formed by said relay optical system into a plurality of portions;

image formation optical systems for receiving light beams from said pupil dividing means so as to form a plurality of object images having parallax; and imaging means for picking up object images formed by said image formation optical system;

said relay optical system including a system of relay lenses that satisfies at least one of the following conditions (A1) to (A4):

condition (A1): $\phi^2/L > 0.573$ condition (A2): $\phi/\Phi > 0.71$ condition (A3): $\phi/\Phi \geq 0.72$ condition (A4): $\phi/L > 0.078$ where $\phi$ denotes an outer diameter of said system of relay lenses, L denotes a relay length of said system of relay lenses, and $\Phi$ denotes an outer diameter of said insertional part.

14. A stereoscopic-vision endoscope characterized in that an intermediate image of an object to be observed is formed on imaging surfaces of two imaging devices by means of two image formation lenses each having a brightness stop in front thereof, wherein no interposing lenses exist between the intermediate image and each brightness stop.

* * * * *